US010589112B2

(12) United States Patent
Quan et al.

(10) Patent No.: US 10,589,112 B2
(45) Date of Patent: Mar. 17, 2020

(54) DYNAMIC ENERGY SELECTION FOR DEFIBRILLATION

(71) Applicant: ZOLL Medcial Corporation, Chelmsford, MA (US)

(72) Inventors: Weilun Quan, Dracut, MA (US); Gary A. Freeman, Waltham, MA (US)

(73) Assignee: ZOLL Medical Corporation, Chelmsford, MA (US)

(*) Notice: Subject to any disclaimer, the term of this patent is extended or adjusted under 35 U.S.C. 154(b) by 0 days.

(21) Appl. No.: 15/608,526

(22) Filed: May 30, 2017

(65) Prior Publication Data
US 2017/0348538 A1 Dec. 7, 2017

Related U.S. Application Data

(63) Continuation of application No. 14/736,149, filed on Jun. 10, 2015, now abandoned, and a continuation of
(Continued)

(51) Int. Cl.
A61N 1/39 (2006.01)
A61B 5/04 (2006.01)
(Continued)

(52) U.S. Cl.
CPC .......... A61N 1/3987 (2013.01); A61B 5/0402 (2013.01); A61B 5/04011 (2013.01);
(Continued)

(58) Field of Classification Search
CPC .. A61N 1/3987; A61N 1/3925; A61N 1/3993; A61H 31/004
See application file for complete search history.

(56) References Cited

U.S. PATENT DOCUMENTS 5,077,667 A 12/1991 Brown et al.
5,092,341 A 3/1992 Kelen
(Continued)

FOREIGN PATENT DOCUMENTS

WO WO 2011/100534 8/2011
WO WO 2012/059846 5/2012
(Continued)

OTHER PUBLICATIONS

Chaudhry, Fand A., A Novel Resuscitation Algorithm Using Waveform Analysis and End-Tidal Carbon Dioxide Pressure for Ventricular Fibrillation, University of Arizona, Biomedical Engineering Interdisciplinary Program, 2011, 39 pages.
(Continued)

Primary Examiner — Joseph M Dietrich
(74) Attorney, Agent, or Firm — Fish & Richardson P.C.

(57) ABSTRACT

In an aspect, a system for treating a patient in cardiac arrest is described and includes memory, one or more electronic ports for receiving signals from sensors for obtaining indications of an electrocardiogram (ECG) of the patient, one or more sensors for obtaining a transthoracic impedance of the patient, and a patient treatment module executable on one or more processing devices that is configured to generate, from the ECG, transform values that represent magnitudes of two or more frequency components of the ECG, and modify, based on at least one transform value, at least one shock delivery parameter.

26 Claims, 8 Drawing Sheets

Related U.S. Application Data application No. 14/656,812, filed on Mar. 13, 2015, now abandoned.

(60) Provisional application No. 62/010,202, filed on Jun. 10, 2014, provisional application No. 61/953,194, filed on Mar. 14, 2014.

(51) Int. Cl.
*A61B 5/00* (2006.01)
*A61B 5/0402* (2006.01)
*A61B 5/053* (2006.01)
*A61H 31/00* (2006.01)

(52) U.S. Cl.
CPC ............ *A61B 5/053* (2013.01); *A61B 5/4836* (2013.01); *A61H 31/004* (2013.01); *A61N 1/3906* (2013.01); *A61N 1/3937* (2013.01); *A61N 1/3993* (2013.01); *A61B 5/7257* (2013.01); *A61H 31/005* (2013.01); *A61H 31/006* (2013.01); *A61H 31/007* (2013.01); *A61H 2230/045* (2013.01); *A61N 1/3968* (2013.01)

(56) References Cited

U.S. PATENT DOCUMENTS

| | | | |
|---|---|---|---|
| 5,741,304 | A | 4/1998 | Patwardhan et al. |
| 5,957,856 | A | 9/1999 | Weil et al. |
| 6,171,257 | B1 | 1/2001 | Weil |
| 6,224,562 | B1 | 5/2001 | Lurie et al. |
| 6,760,621 | B2 | 7/2004 | Walcott |
| 6,813,517 | B2 | 11/2004 | Daynes et al. |
| 7,269,454 | B2 | 9/2007 | Sherman |
| 7,593,772 | B2 | 9/2009 | Sherman |
| 7,774,060 | B2 | 8/2010 | Westenkow |
| 7,813,791 | B1 | 10/2010 | Gill |
| 7,831,299 | B2 | 11/2010 | Tan et al. |
| 7,920,917 | B2 | 4/2011 | Kelly |
| 8,165,671 | B2 | 4/2012 | Freeman et al. |
| 8,868,179 | B2 | 10/2014 | Quan et al. |
| 8,948,859 | B2 | 2/2015 | Freeman et al. |
| 9,180,304 | B2 | 11/2015 | Quan et al. |
| 9,186,521 | B2 | 11/2015 | Quan et al. |
| 9,480,853 | B2 | 11/2016 | Quan et al. |
| 9,579,515 | B2 | 2/2017 | Quan et al. |
| 9,592,402 | B2 | 3/2017 | Quan et al. |
| 9,782,093 | B2 | 10/2017 | Quan et al. |
| 9,907,477 | B2 | 3/2018 | Quan et al. |
| 2002/0026229 | A1 | 2/2002 | Weil et al. |
| 2002/0133197 | A1 | 9/2002 | Snyder et al. |
| 2002/0138106 | A1 | 9/2002 | Chiristini et al. |
| 2003/0055460 | A1 | 3/2003 | Owen et al. |
| 2004/0039419 | A1 | 2/2004 | Stickney et al. |
| 2004/0116969 | A1 | 6/2004 | Owen |
| 2004/0215271 | A1 | 10/2004 | Sullivan |
| 2005/0080828 | A1 | 5/2005 | Johnson |
| 2005/0245974 | A1 | 11/2005 | Sherman |
| 2005/0267536 | A1 | 12/2005 | Freeman et al. |
| 2006/0025824 | A1 | 2/2006 | Freeman |
| 2006/0116724 | A1 | 6/2006 | Snyder |
| 2007/0060785 | A1 | 3/2007 | Freeman et al. |
| 2007/0100381 | A1 | 5/2007 | Snyder et al. |
| 2008/0145827 | A1 | 6/2008 | Strand et al. |
| 2008/0208070 | A1 | 8/2008 | Snyder et al. |
| 2009/0270930 | A1 | 10/2009 | Walker |
| 2010/0268059 | A1 | 10/2010 | Ryu et al. |
| 2010/0298899 | A1 | 11/2010 | Donnelly et al. |
| 2011/0021938 | A1 | 1/2011 | Anderson et al. |
| 2011/0034816 | A1 | 2/2011 | Tan et al. |
| 2011/0202100 | A1 | 8/2011 | Tan et al. |
| 2011/0202101 | A1 | 8/2011 | Tan et al. |
| 2011/0295127 | A1 | 12/2011 | Sandler et al. |
| 2012/0010543 | A1 | 1/2012 | Johnson et al. |
| 2012/0046706 | A1 | 2/2012 | Anderson et al. |
| 2012/0191024 | A1 | 4/2012 | Halperin et al. |
| 2012/0226178 | A1 | 9/2012 | Freeman et al. |
| 2013/0138168 | A1 | 5/2013 | Quan et al. |
| 2013/0190634 | A1 | 7/2013 | Phillips |
| 2013/0218057 | A1 | 8/2013 | Jorgenson |
| 2014/0005738 | A1 | 1/2014 | Jorgenson et al. |
| 2014/0144181 | A1 | 5/2014 | Fogt et al. |
| 2014/0236030 | A1 | 8/2014 | Tan et al. |
| 2014/0277224 | A1 | 9/2014 | Quan et al. |
| 2014/0277228 | A1 | 9/2014 | Quan et al. |
| 2015/0126885 | A1 | 5/2015 | Freeman et al. |
| 2015/0257715 | A1 | 9/2015 | Quan et al. |
| 2015/0352367 | A1 | 12/2015 | Quan et al. |
| 2015/0352369 | A1 | 12/2015 | Quan et al. |
| 2016/0023010 | A1 | 1/2016 | Quan et al. |
| 2016/0082278 | A1 | 3/2016 | Quan et al. |
| 2017/0209706 | A1 | 7/2017 | Quan et al. |

FOREIGN PATENT DOCUMENTS

| | | |
|---|---|---|
| WO | WO 2012/072518 | 6/2012 |
| WO | WO 2013/071280 | 5/2013 |

OTHER PUBLICATIONS

Chinese Office Action, CN Application 201480027256.X, dated May 30, 2016, 8 pages.
Compos et al., "An Up-Down Bayesian, Defibrillation Efficacy Estimator", PACE—Pacing and Clinical Electrophysiology, Blackwell Futura Publishing, Malden, MA, US, vol. 20, No. 5, Part 01, May 1, 1997, pp. 1292-1300.
European Search Report, 14768658.8, dated Feb. 12, 2016, 10 pages.
Extended European Search Report, PCT/US2012/065779, dated Aug. 14, 2015, 7 pages.
Extended European Search Report, European Patent Application No. 13804051.4, dated Feb. 4, 2016, 9 pages.
Huang et al, "Quantification of activation patterns during ventricular fibrillation in open-chest porcine left ventricle and septum", Heart Rhythm Elsevier, US, vol. 2, No. 7, Jul. 1, 2005, pp. 720-728.
International Search Report and Written Opinion, PCT/US2012/64779, dated Feb. 1, 2013, 8 pages.
International Search Report and Written Opinion, PCT/US2014/027431, dated Aug. 11, 2014, 14 pages.
International Search Report and Written Opinion, PCT/US2014/27514, dated Aug. 11, 2014, 8 pages.
International Search Report and Written Opinion, PCT/US2014/27658, dated Aug. 25, 2014, 19 pages.
International Search Report and Written Opinion, PCT/US2015/35174, dated Sep. 17, 2015, 13 pages.
International Search Report and Written Opinion, PCT/US2015/35189, dated Nov. 3, 2015, 20 pages.
International Search Report and Written Opinion from corresponding PCT/US2013/44750 dated Sep. 20, 2013.
Lee, Seungyup, "Mapping the Characteristics of Atrial Activation Patterns During Atrial Fibrillation," Case Western Reserve University: Department of Biomedical Engineering, Jan. 2013, 34 pages.
Povoas et al., "Predicting the success of defibrillation by electrocardiographic analysis," Resuscitation 53(1):77-82 (2002).
Supplementary European Search Report, European Patent Application No. 13804051.4, dated Feb. 23, 2016, 10 pages.
Watson et al., "Rapid Communication; Wavelet transform-based prediction of the likelihood of successful defibrillation for patients exhibiting ventricular fibrillation; Rapid Communication", Measurement Science and Technology, IOP, Bristol, GB, vol. 16, No. 10, Oct. 1, 2005, pp. L1-L6.
Supplementary European Search Report, dated Nov. 4, 2016 for EP Application No. 14768107.6, 3 pages.
International Search Report and Written Opinion dated Jun. 10, 2016 in international application No. PCT/US2016/023992, 7 pgs.
International Preliminary Report on Patentability issued in international application No. PCT/US2016/023992, dated Sep. 26, 2017, 9 pages.

(56) References Cited

OTHER PUBLICATIONS

U.S. Office Action in U.S. Appl. No. 15/868,277, dated Jun. 4, 2018, 6 pages.

DYNAMIC ENERGY SELECTION FOR DEFIBRILLATION

CROSS REFERENCE TO RELATED APPLICATIONS

This application is a continuation of U.S. patent application Ser. No. 14/736,149, filed on Jun. 10, 2015, which claims priority to U.S. Provisional Application 62/010,202, filed on Jun. 10, 2014. This application is also a continuation of U.S. patent application Ser. No. 14/656,812, filed on Mar. 13, 2015, which claims priority to U.S. Provisional Application 61/953,194, filed on Mar. 14, 2014. The content of each of the above referenced applications are incorporated herein by reference.

TECHNICAL FIELD

This document relates to cardiac resuscitation systems and techniques.

BACKGROUND

Ventricular fibrillation (VF) is an abnormal heart rhythm (arrhythmia) that causes the heart to lose pumping capacity. If such a problem is not corrected quickly—typically within minutes—the rest of the body loses oxygen and the person dies. Therefore, prompt care of a person undergoing VF can be key to a positive outcome for such a person.

One common way to treat ventricular fibrillation is through the use of an electrical defibrillator that delivers a relatively high-voltage shock to the heart in order to force it back to a normal, consistent, and strong rhythm. People who have had previous problems with ventricular fibrillation may be implanted with an automatic defibrillator, or be provided a wearable defibrillator, that constantly monitors the condition of their heart and applies a shock when necessary. Other people may be treated using a portable external defibrillator, such as in a hospital or by emergency medical technicians, or via an automatic external defibrillator (AED) of the kind that is frequently seen in airports, public gymnasiums, and other public spaces. Defibrillation may be delivered in coordination with cardiopulmonary resuscitation (CPR), which centers around the provision of repeated compressions to a victim's chest, such as by a rescuer pressing downward repeatedly with the palms of the hands, or via an automatic mechanical compression device.

SUMMARY

This document describes systems and techniques that may be used to adjust the manner in which shocks are delivered to a person suffering from VF. The techniques discussed here take into account a number of input signals in determining whether a shock should be delivered and how it should be delivered. Generally, the input signals are patient-dependent, in that they are measured from a patient at the time of a rescue event, e.g., by electrodes from a portable defibrillator that have been attached to the patient's skin. One such signal is an amplitude spectrum area (AMSA) value, where the AMSA transform value is a numerical value that is based on the sum of the magnitude of a weighted frequency distribution from the signal, e.g., between 3 and 48 Hz. Such AMSA transform value can be used, alone or in combination with other signals, to determine a likelihood that a shock will succeed in defibrillating a patient if it is currently delivered, and also to determine an energy level to deliver with the shock.

As to delivered energy levels, generally, a patient's AMSA transform values decrease as time goes on in a VF event without achieving defibrillation, and energy needed for a successful defibrillation goes up. Thus, a defibrillator may be programmed to select energy levels for charging capacitors and delivering shocks, where the energy levels increase as the measured AMSA level decreases. In other implementations, the selected energy may be a function of a ratio between AMSA of other electrocardiograph predictor, and trans-thoracic impedance (TTI) measured for the patient.

The energy level of delivered shocks may by increased automatically by a defibrillator or higher energy levels may be suggested to a rescuer who is selecting energy levels manually, as a VF episode continues. In particular, shocks may be delivered with fewer joules early in an event and may increase as time passes, or increases with each shock that is delivered, or both. Whether the energy increase is made automatically or as part of a suggestion to the rescuer may depend on whether the defibrillator is operating in a manual mode (where the rescuer is presumed to have expertise to select his or her own energy level) or an automatic mode (where the rescuer is presumed to need direct assistance).

Upon a defibrillator making a determination that a shock to be delivered currently will succeed in defibrillating the patient (i.e., determining a likelihood of future success for defibrillating the patient), the defibrillator may provide an indication to a rescuer about such a determination, and may also provide an indication of a planned energy for the shock. For example, the defibrillator may only allow a shock to be performed when the indication is sufficiently positive (e.g., over a set percentage of likelihood of success)—and may only provide a "ready for shock" light or other indication in such a situation. Also, a defibrillator may provide a display—such as a graphic that shows whether defibrillation will likely succeed (e.g., above a predetermined threshold level of likelihood of success) or provide a number (e.g., a percentage of likelihood of success) or other indication (e.g., a grade of A, B, C, D, or F) so that the rescuer can determine whether to apply a shock. The display may also show the energy level that the shock will be delivered at, and the rescuer in appropriate circumstance may be able to change the energy level before delivering the shock (and potentially before charging the capacitor or capacitors, if such charging occurs late in the process).

In certain implementations, such systems and techniques may provide one or more advantages. For example, determinations of whether a shock should be provided or what advice to provide a rescuer based on AMSA transform values can be made from variables that are measured for a patient for other purposes (e.g., TTI and ECG readings). Also, energy levels can be selected that are determined a priori to maximize that likelihood of successful defibrillation. The AMSA transform values can be improved with respective to their predictive qualities by actions such as monitoring ECG vectors and performing vectorized FFT operations to produce an improved AMSA value. As a result, a patient may avoid receiving an ineffective shock, and then having to wait another cycle for another shock (which may end up being equally ineffective), and avoid the physical harm caused by any delivered shocks. And a system may guide the rescuer in providing the actions that are currently best for the patient, whether that involves delivering a shock, providing deep chest compressions, providing progressive chest compressions, or otherwise caring for the patient. Alternatively, the techniques described here may be implemented by a system that provides chest compressions automatically and mechanically throughout the course of a cardiac event. Such a process may, therefore, result in the patient returning to normal cardiac function more quickly and with less stress on his or her cardiac system, which will generally lead to better patient outcomes.

In one implementation, a system for managing care of a person is disclosed and comprises one or more capacitors arranged to deliver a defibrillating shock to a patient; one or more electronic ports for receiving a plurality of signals from sensors for obtaining indications of an electrocardiogram (ECG) for the patient; and a patient treatment module executable on one or more computer processors using code stored in non-transitory media and arranged to identify a level of energy to be delivered in a shock to the patient by applying a mathematical computation to current ECG data from the patient and data indicating a present level of trans-thoracic impedance for the patient. The mathematical computation may comprise applying one or more Fast Fourier Transforms (FFTs) to the ECG data, and the FFTs may comprise vectorized FFTs applied to vectors formed by different leads for collecting the ECG data. The mathematical computation can also comprise one or more amplitude spectrum area calculations applied to the ECG data.

In certain aspects, the mathematical computation comprises a mathematical transform from a time domain to a frequency domain on a window of data. The window may be between about one second and about 2 seconds in width, and may be a tapered window for example Tukey, Hann, Blackman-Harris, or Flat Top. Also, the system can be programmed to automatically charge the one or more capacitors to the identified a level of energy to be delivered.

In other aspects, the system is programmed to present to a user the identified level of energy to be delivered, and to permit the user to choose between using the identified level of energy to be delivered or manually selecting a different level of energy to be delivered. The system can also include a visible, audible, or tactile output mechanism arranged to present, to the user, an indication regarding the identified level of energy to be delivered. In addition, the patient treatment module can be arranged to identify the level of energy to be delivered in the shock to the patient by applying the mathematical computation to a ratio correlating the present level of trans-thoracic impedance of the patient and a value derived from the current ECG from the patient. The patient treatment module can also be further arranged to use the current ECG data to determine a likelihood of success from delivering a defibrillating shock with the one or more capacitors to the patient.

In yet other aspects, the system also includes an interlock that prevents a user from delivering a shock unless the determined likelihood of success exceeds a determined value. The system can also include a visible, audible, or tactile output mechanism arranged to present, to a user of the system, an indication regarding the determined likelihood of success from delivering the defibrillating shock with the one or more capacitors to the patient. Moreover, the patient treatment module can comprise an ECG analyzer for generating an amplitude spectrum area (AMSA) value using the transform.

In another implementation, a method is disclosed for managing care of a person. The method comprises monitoring, with an external defibrillator, electrocardiogram (ECG) data from a person receiving emergency cardiac assistance; performing a mathematical transformation of the ECG data from a time domain to a frequency domain using a window of the ECG data in the time domain; and determining a level of energy to be delivered using at least the mathematical transformation of the ECG data and data indicating a present level of trans-thoracic impedance for the patient. The method can also comprise displaying to a user of the external defibrillator a numeric value of the determined level of energy, the mathematical transformation can comprise applying one or more Fast Fourier Transforms (FFTs) to the ECG data, and the FFTs can comprise vectorized FFTs applied to vectors formed by different leads for collecting the ECG data.

In some aspects, the mathematical transformation comprises one or more amplitude spectrum area calculations applied to the ECG data. Also, the window of ECG data can comprise a window that is between about one second and about two seconds in width, and the window can be a tapered window selected from a group comprising Tukey, Hann, Blackman-Harris, and Flat Top. The method can additionally include automatically charging one or more capacitors of the external defibrillator to the identified a level of energy to be delivered. Moreover, the method can include presenting to a user of the defibrillator the identified level of energy to be delivered, and permitting the user to choose between using the identified level of energy to be delivered or manually selecting a different level of energy to be delivered.

In yet other aspects, the method can also include presenting to the user a visual, audible, or tactile indication regarding the identified level of energy to be delivered. In addition, the method can comprise determining the level of energy to be delivered by applying the mathematical transformation to a determined trans-thoracic impedance of the patient. The method can also comprise identifying the level of energy to be delivered by applying the mathematical transformation to a ratio correlating the determined trans-thoracic impedance of the patient and a value derived from the current ECG from the patient, and using the current ECG data to determine a likelihood of success from delivering a defibrillating shock with the one or more capacitors to the patient. In addition, the method can include preventing a user of the defibrillator from delivering a shock with the defibrillator unless the determined likelihood of success exceeds a determined value.

In an aspect, a system for treating a patient in cardiac arrest is described and includes memory, one or more electronic ports for receiving signals from sensors for obtaining indications of an electrocardiogram (ECG) of the patient, one or more sensors for obtaining a transthoracic impedance of the patient, and a patient treatment module executable on one or more processing devices that is configured to generate, from the ECG, transform values that represent magnitudes of two or more frequency components of the ECG, and modify, based on at least one transform value, at least one shock delivery parameter.

In another aspect, a system for treating a patient in cardiac arrest is described and includes memory, one or more electronic ports for receiving signals from sensors for obtaining indications of an electrocardiogram (ECG) the patient, one or more sensors for obtaining a transthoracic impedance of the patient, and a patient treatment module executable on one or more processing devices that is configured to generate transform values that represent magnitudes of two or more frequency components of the ECG, determine the viability of future therapeutic actions based at least in part on the transform values and the transthoracic impedance, and provide a treatment determination based on the viability determination.

In a further aspect, a system for monitoring the physiological status of a patient in cardiac arrest is described and includes memory, one or more electronic ports for receiving signals from sensors for obtaining indications of a vectorcardiograph (VCG) for the patient, and a patient treatment module executable on one or more processing devices that is configured to generate transform values for a time segment of VCG, wherein the transform values represent magnitudes of two or more frequency components of the VCG, and are indicative of a likelihood of success of a future therapeutic action.

In another aspect, one or more machine-readable storage devices are described that have encoded thereon machine readable instructions for causing one or more processors to perform operations comprising receiving signals indicative of an electrocardiogram (ECG) of a patient, obtaining a transthoracic impedance of the patient, generating, from the ECG, transform values that represent magnitudes of two or more frequency components of the ECG, and modifying, based on at least one transform value, at least one shock delivery parameter.

In a further aspect, one or more machine-readable storage devices are described that have encoded thereon machine readable instructions for causing one or more processors to perform operations comprising receiving signals indicative of an electrocardiogram (ECG) of a patient, obtaining a transthoracic impedance of the patient, generating transform values that represent magnitudes of two or more frequency components of the ECG, determining the viability of future therapeutic actions based at least in part on the transform values and the transthoracic impedance, and providing a treatment determination based on the viability determination.

In another aspect, one or more machine-readable storage devices are described that have encoded thereon machine readable instructions for causing one or more processors to perform operations comprising receiving signals indicative of a vectorcardiograph (VCG) for a patient, and generating transform values for a time segment of VCG, wherein the transform values represent magnitudes of two or more frequency components of the VCG, and are indicative of a likelihood of success of a future therapeutic action.

In another aspect, a method is described that includes receiving signals indicative of an electrocardiogram (ECG) of a patient, obtaining a transthoracic impedance of the patient, generating, from the ECG, transform values that represent magnitudes of two or more frequency components of the ECG, and modifying, based on at least one transform value, at least one shock delivery parameter.

In a further aspect, a method is described that includes receiving signals indicative of an electrocardiogram (ECG) of a patient, obtaining a transthoracic impedance of the patient, generating transform values that represent magnitudes of two or more frequency components of the ECG, determining the viability of future therapeutic actions based at least in part on the transform values and the transthoracic impedance, and providing a treatment determination based on the viability determination.

In an additional aspect, a method is described that includes receiving signals indicative of a vectorcardiograph (VCG) for a patient, and generating transform values for a time segment of VCG, wherein the transform values represent magnitudes of two or more frequency components of the VCG, and are indicative of a likelihood of success of a future therapeutic action.

Other features and advantages will be apparent from the description and drawings, and from the claims.

DETAILED DESCRIPTION

In general, defibrillation is a common treatment for various arrhythmias, such as VF. However, there can be undesired side effects (e.g., heart tissue damage, skin burns, etc.) that follow an electrical shock. Other undesired side effects include unnecessary interruptions of chest compressions when a shock needs to be delivered. Added to this, the effectiveness of defibrillation can fall generally over the elapsed time of a VF episode—where an episode may be measured from the time when a victim first starts feeling symptoms of cardiac arrest or loses consciousness and falls down. (Generally, the time from onset of a lethal VF episode and unconsciousness is relatively short, on the order of less than one-half minute.) It is therefore desirable to predict whether defibrillation will be successful in restoring a regular heartbeat following onset of an arrhythmic episode, determine a proper energy level for a shock, and/or to determine how long it has been since a cardiac event started or what stage of the event the patient is in (e.g., a first, second, or third stage or phase).

Predictions about likely effectiveness of a shock (which may be termed as an "indicator of success," a "success indication," or a "determination" and "indication of a likelihood of success") may cause a defibrillating shock to not be provided when the chance of successful defibrillation is low. Instead, the shock may be provided when its odds of succeeding are relatively high, and can be provided at an energy level that maximizes those odds of success.

Figure 1:
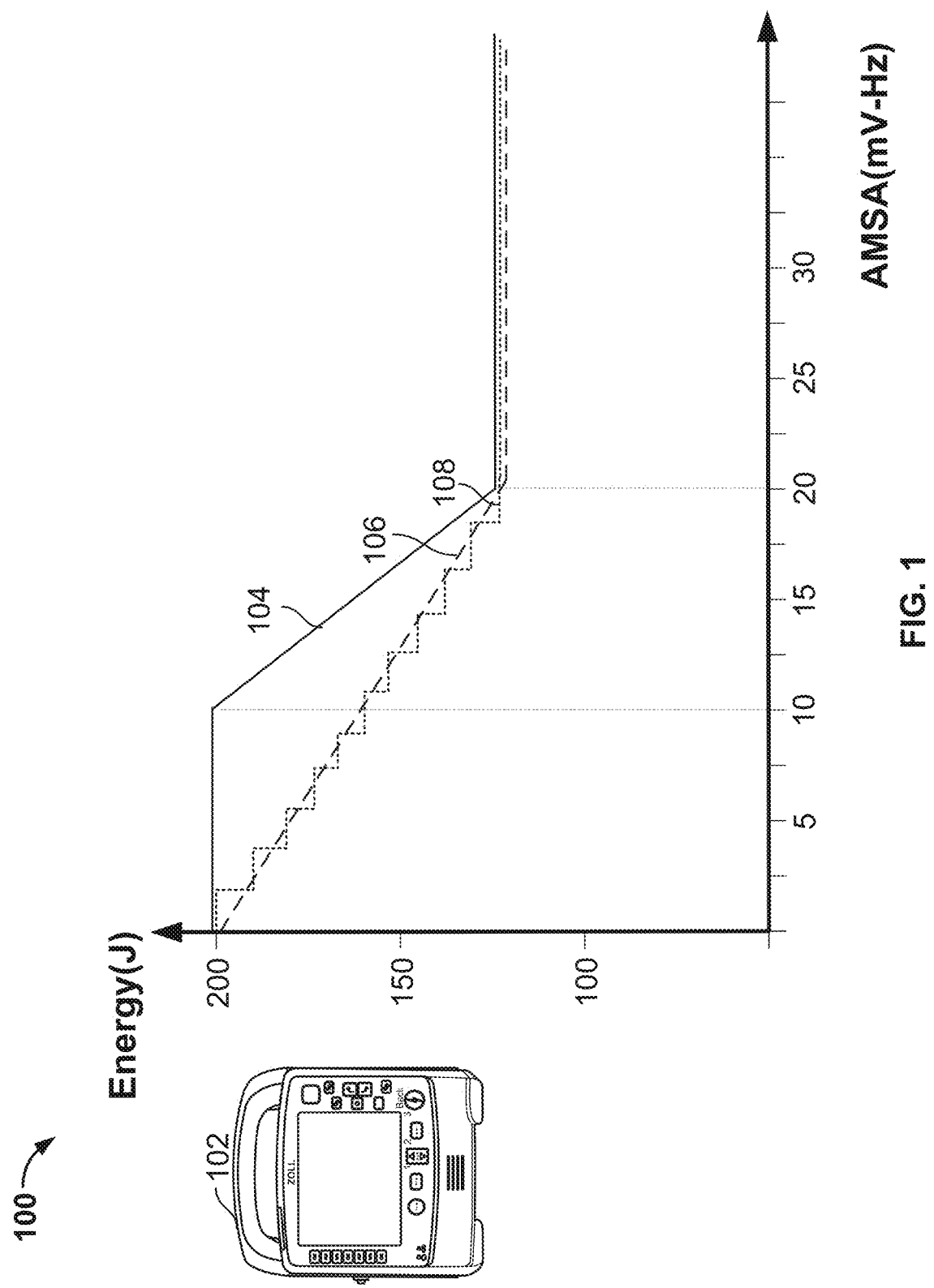
FIG. 1 shows a relationship between AMSA and shock energy that may be implemented by a portable defibrillator.

FIG. 1 shows a relationship between AMSA and shock energy that may be implemented by a portable defibrillator. In the figure, a graph 100 shows identified relationships between AMSA transform values (expressed as mV-Hz according to common practice) and energy (expressed in Joules, as is also common practice) levels that have been determined to be needed to successfully defibrillate a patient at such corresponding AMSA transform values (e.g., above a predetermined predicted likelihood of success value). The values shown here may be programmed into a medical device like a defibrillator, where the AMSA value is treated as an independent variable (along with potentially other inputs, such as TTI), and the energy level is the dependent variable. In particular, an AMSA value or similar value (e.g., that is based on amplitudes in an ECG signal for a patient) may be computed from a patient's ECG data, and the medical device may select an energy level based on the computed AMSA value (and perhaps based on additional values, such as by blending the multiple inputs together in a weighted manner). The energy value may be applied automatically in charging capacitors for delivering a shock to a patient, or may be displayed or otherwise presented to a rescuer, with the rescuer able to override the suggested energy level with a manually entered energy level, followed by the rescuer choosing to deliver the shock.

Three example relationships are shown between AMSA transform values and energy output values in this example. Generally, each of the representations indicate that the energy needed to achieve a successful defibrillation falls as AMSA rises. The three examples show programming for a defibrillator 102 by which the relationship between computed AMSA transform values and the energy computed by the defibrillator has different partially-linear relationships with AMSA (though non-linear relationships may also be employed). Such relationships may be determined by analyzing data collected by defibrillators in-the-field for past rescue events, and identifying AMSA for patients from such events (for both successful and unsuccessful delivered shocks), energy levels for such events, and defibrillation outcomes. Standard statistical techniques can then be applied to determine relationships between AMSA and energy for successful defibrillation and unsuccessful defibrillation. Other factors, as indicated in more detail below, may also be used in determining appropriate energy levels, such as trans-thoracic impedance (TTI), patient body size (e.g., weight or surface area, whether actual or estimated) and pharmacological history for the patient, either outside of the present VF episode or as part of the episode.

Stepped trace 108 generally shows increasing energy with decreasing AMSA transform values. The increases in energy may be stepped, such as in 1, 2, 5, or 10 Joule steps at appropriate AMSA transform values (every 0.5, 1, 2, 3, 4, or 5 steps of AMSA transform value). Such a trace 108 may be implemented by formula or look-up table, where the look-up table correlates the particular discrete values for AMSA shown here to an output for the multiple discrete levels of energy shown here.

In certain implementations, the energy may be flat for a range of AMSA transform values, but linearly changing for another range of AMSA transform values. For example, the energy can be flat at high and low AMSA transform values, and sloped in the middle. Trace 104 shows such a relationship for energy that will be computed by the defibrillator as changing by such a flat-slope-flat function. In this example, energy is consistent for a large range of AMSA transform values and then changes linearly for a mid-range of AMSA transform values, and is steady again for another range of AMSA transform values.

Trace 102 is similar to trace 104 in that it has a sloped portion and a flat portion. However, trace 102 is sloped starting immediately at low AMSA levels until it flattens at a particular AMSA transform value (here, 20 mV-Hz).

The particular traces shown here are provided for explication only, and other relationships may be programmed into a medical device such as a defibrillator, and the computation of appropriate energy may be based on multiple factors, in addition to an AMSA or similar value derived from ECG data. For example, a relationship may include both linear and non-linear portions if such is what data from past usage indicates is the best approach to having future defibrillators select output energy for shocks. Also, as discussed further next, the computation of output energy may depend on multiple inputs, in addition to AMSA or other ECG amplitude-related criterion, and the relationship between inputs and energy output may be determined in a variety of manners, including multi-dimensional regression analysis that can then be represented by data structure or formula for computing energy output in future devices.

Figure 2A:
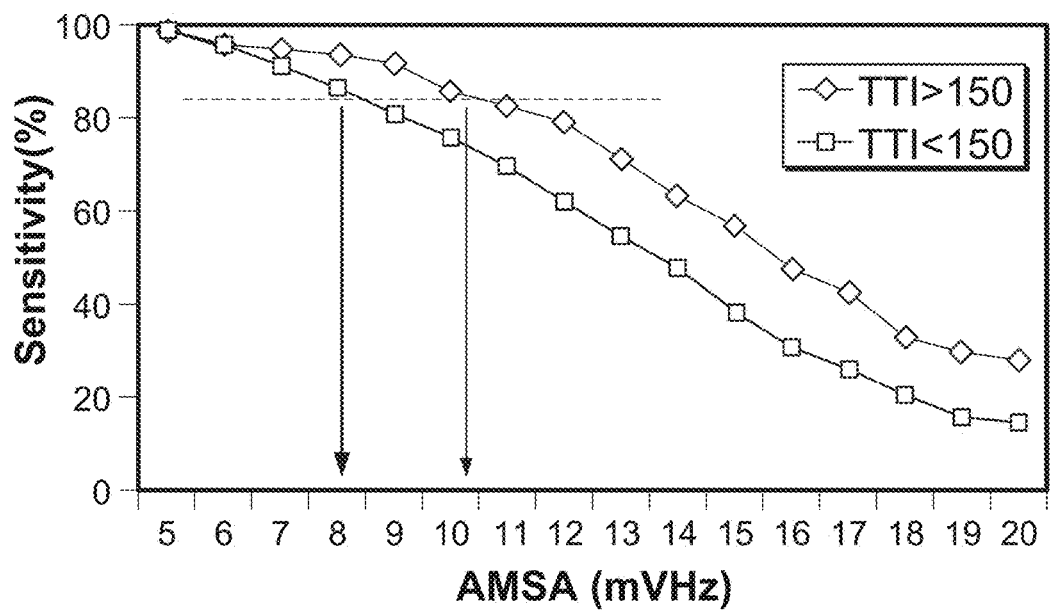
FIGS. 2A and 2B are graphs showing relationships between sensitivity and specificity, and AMSA threshold values for groups of patients.

FIG. 2A shows a plot of sensitivity (%) versus AMSA threshold (mv-Hz) for a first set of subjects having a trans-thoracic impedance (TTI) measured greater than 150 ohms, and a second set of subjects having a trans-thoracic impedance measured less than 150 ohms. The data shows the influence of TTI on the prediction accuracy of AMSA for shock success at different threshold values as presented in sensitivity and specificity. Such values may be incorporated with AMSA transform values so as to select an output energy for a defibrillator, where the output energy is both a function of AMSA (or other ECG based shock prediction value) and of TTI. A gain factor may be used to adjust for variations in TTI so as to maintain substantially equal levels of performance of AMSA with regard to assessing the likelihood of viability of future therapeutic actions, e.g., the viability of delivering a defibrillating shock. For example, referring again to FIG. 2A, the AMSA transform values for TTI<150 Ohms may be multiplied by a gain factor of 1.17 so that the two curves overlap more closely. In some implementations, a linear or non-linear regression analysis may be performed to determine the relationship between the optimal AMSA measure, which has as inputs to the regression equation the TTI measure, and the raw AMSA reading. In some implementations, the viability of a future therapeutic action may be expressed as a probability, e.g. 0-100%, and the probability may be adjusted by the TTI measure, for instance, using regression methods, table lookup or neural networks. In some implementations, complex relationships, such as depicted in FIG. 2B, may require table lookup or non-linear regression to be adjusted for effects of TTI.

The data was obtained by collecting data from defibrillators used in real rescue events from multiple emergency medical services in the United States through regular field case submission to ZOLL Medical Corporation, and where individual personal identifying information could not be determined from the gathered data. All reporting parties used ZOLL automatic external defibrillators that included current-based impedance compensation. The sampling rate for ECG data was 250 Hz, and analysis was performed on a selection of an episode of 2.05 seconds (512 data points) ending at 0.5 seconds before each shock attempt. Shock success was defined as an organized rhythm for a minimum of 30 seconds, starting 60 seconds after the delivered shock, and with a rate of 40 beats per minute or greater. A total of 1292 shocks (305 successful) form 580 patients with VF were included in the analysis. AMSA. The TTI was measure at shocking pads placed on each respective subject.

As shown by the comparative data, a patient's TTI affects the predictability of AMSA by shifting the threshold upward for a given sensitivity or specificity value. AMSA transform value was significantly higher when the TTI was greater than 150 ohm (11.6±8.9 vs. 9.8±7.1, p=0.002) as compared with those shocks with TTI less than 150 ohm. The AMSA threshold value was increased from 8.2 mvHz to 10.3 mvHz when sensitivity was set to 85%. Such information can be used to provide a real-time adjustment mechanism, like those discussed above, that adjusts an AMSA threshold for predicting likelihood of shock success or otherwise taking into account the real-time measured TTI so as to affect the reported likelihood in a manner that makes it more accurate.

Figure 2B:
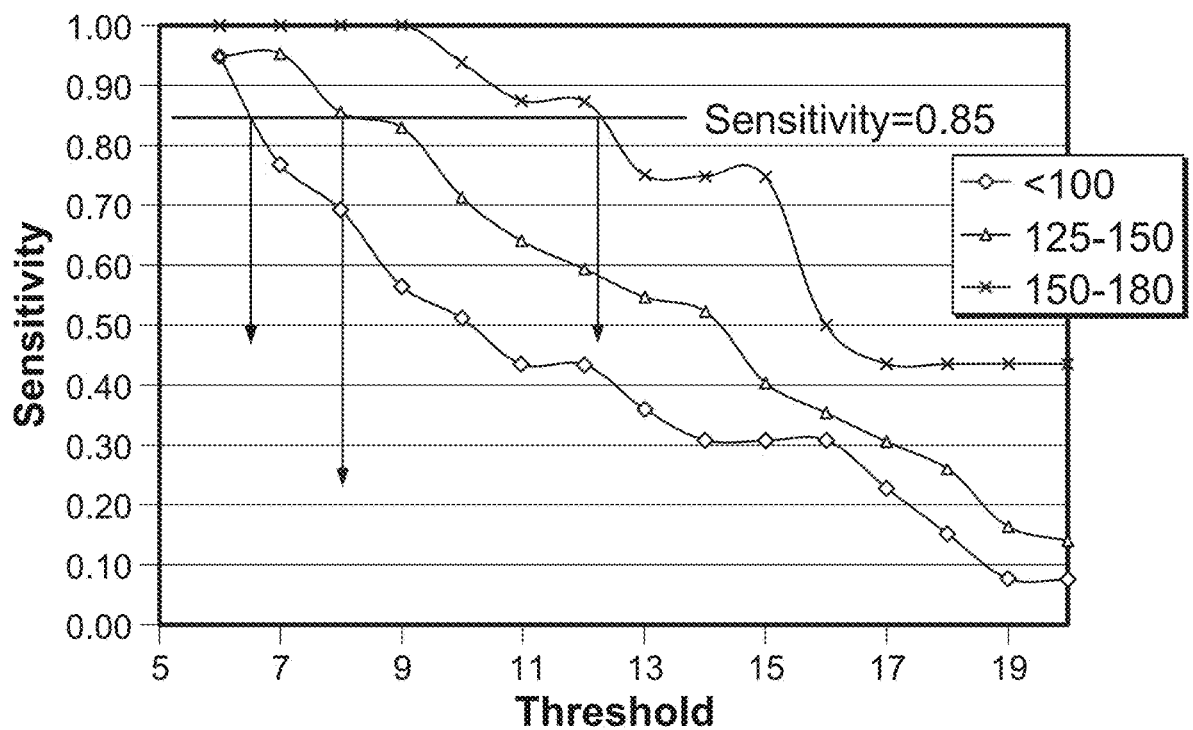

FIG. 2B shows a plot of specificity (%) versus AMSA threshold (mv-Hz) for a first set of subjects having a trans-thoracic impedance measured less than 150 ohms, a second set of subjects having a trans-thoracic impedance greater than 150 ohms. The tested subjects and data collection were the same as for the graph in FIG. 2A. As shown by the comparative data, AMSA threshold generally increases, for a given specificity, with increasing trans-thoracic impedance. For example specificity at a threshold of 85% was 11.8 mvHz for TTI<150 ohms, and 14.2 mvHz for TTI>150 ohms. Again, analysis of such data may be used in programming devices to provide predictions of likelihood of shock success, or to disable or enable the ability to shock a particular patient, based on calculated AMSA transform values.

Thus, in an implementation, the data structure can be established, and when a shockable rhythm is determined to exist for a patient (e.g., via ongoing analysis of ECG data from the patient), AMSA and other inputs or "signals" can be computed. Those inputs may then be used to compute an energy level to charge the defibrillator capacitor or capacitors to, in addition to other computations (e.g., a computation of a likelihood that a shock, if currently delivered, will succeed in defibrillating the patient).

The likelihood of shock success can depend upon a number of factors, relationships between or among factors, etc. For example, shock energy levels, delivery techniques, etc. may be defined based upon one or more quantities that use AMSA transform values. For example, AMSA transform values may be used to define regions that employ different energy levels, delivery techniques, etc. such as escalating energy levels for subsequent shocks.

In one study data was collected and analyzed from 1219 shocks from 543 patients with VF. ECG recordings, sampled at 250 Hz, were digitized and reviewed. Episodes of approximately two seconds (e.g., 2.05 seconds or 512 data points) that terminated a half second before a shock attempt were analyzed. Shock success was defined as an organized rhythm that was present for a minimum of 30 seconds, started within 60 seconds after the shock, and had a rate of 40 beats per minute or larger.

Figure 2C:
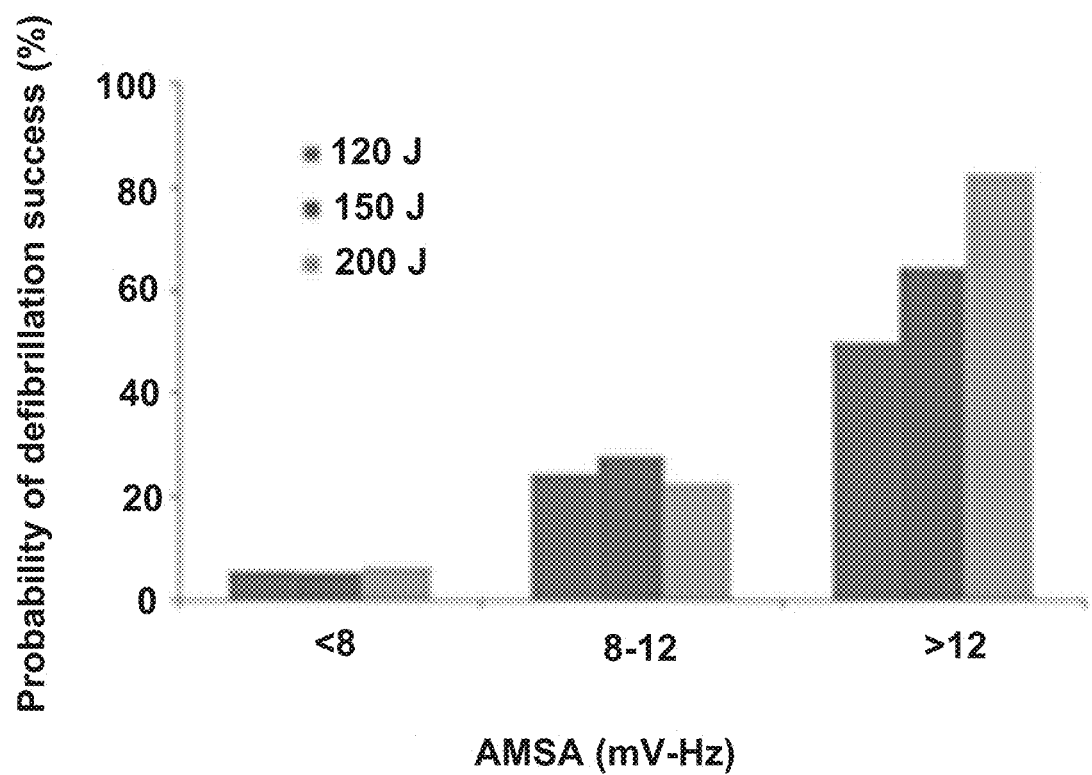
FIG. 2C is a graph showing relationships between AMSA transform values and the probability of defibrillation success.

Using an escalating defibrillation energy protocol (with energy levels stepping from 120 Joules (J) to 150 J and to 200 J), shock success increased with each step for AMSA transform values of 12 mV-Hz or greater (e.g., 50.0% success for 120 J, 64.6% success for 150 J and 82.5% shock success for 200 J). For instances of lower AMSA transform values, below 12 mV-Hz, shock success rates did not significantly improve for the escalation steps (e.g., 9.3% success for 120 J, 12.4% for 150 J and 10.4% for 200 J). Through data analysis (e.g., using multivariable logistic regression), shock success for higher AMSA transform values (e.g., 12 mV-Hz and above) can depend upon the energy level (e.g., higher energy levels may demonstrate improved success) while lower AMSA transform values (e.g., below 12 mV-Hz) may solely depend on the AMSA transform values and be somewhat independent of escalating energy levels. Referring to FIG. 2C, for AMSA transform values larger than 12 mV-HZ, improvement in the probability of success is graphically depicted.

One or more regions may be defined, for example using an AMSA transform value, and different shock protocols can be employed for each region. A single AMSA transform value (e.g., 12 mV-Hz) can define the upper boundary of a lower AMSA transform value region (e.g., values below 12 mV-Hz) and also provide the lower boundary of another region that includes equivalent and larger AMSA transform values (e.g., values of 12 mV-Hz and above). When operating within the first region (e.g., for AMSA transform values below 12 mV-Hz), a fixed low energy level protocol can be employed (e.g., the energy level used for an initial shock is also used for subsequent shocks). For operating in the second region (e.g., when an AMSA value of 12 mV-Hz or larger is measured from a patient), an escalating energy level protocol or a fixed maximum energy protocol can be implemented. An escalating protocol may step the energy levels by using one or more techniques, such as linearly increasing the level with each successive shock (e.g., after an initial shock of 120 J, energy levels of 150 J and then 200 J may sequentially be used). Employing a fixed maximum energy level protocol, an energy level larger than the energy level used for the fixed lower energy level protocol can be implemented. After each shock, another AMSA transform value may be calculated from measurements to determine if the region of operation has changed. By using these regions defined by the AMSA transform value (e.g., 12 mV-Hz), an escalating energy protocol or a fixed maximum energy level protocol may improve defibrillation results when the AMSA transform values is relatively high (e.g., at or above 12 mV-Hz). When low (e.g., below 12 mV-Hz), an escalating energy protocol may not improve defibrillation results and a fixed low energy protocol may perform just as well as the escalating energy protocol. Through real-time AMSA analysis during a CPR, energy selection for defibrillation along with defibrillation timing can be optimized.

In some implementations, other therapeutic and/or shock delivery parameters can be modified based on the transform values. Examples of such therapeutic and/or shock delivery parameters include, but are not limited to: first phase average defibrillation current, defibrillation waveform duration, defibrillation peak voltage, defibrillation waveform rise time, and defibrillation average current. The therapeutic parameters may also include parameters that govern synchronized defibrillation. Synchronized defibrillation is also known as synchronized cardioversion. At low currents or energies, synchronized defibrillation may be beneficial for ECG waveforms with AMSA transform values higher than a threshold (e.g. AMSA transform values in excess of 18 to 20).

Figure 3:
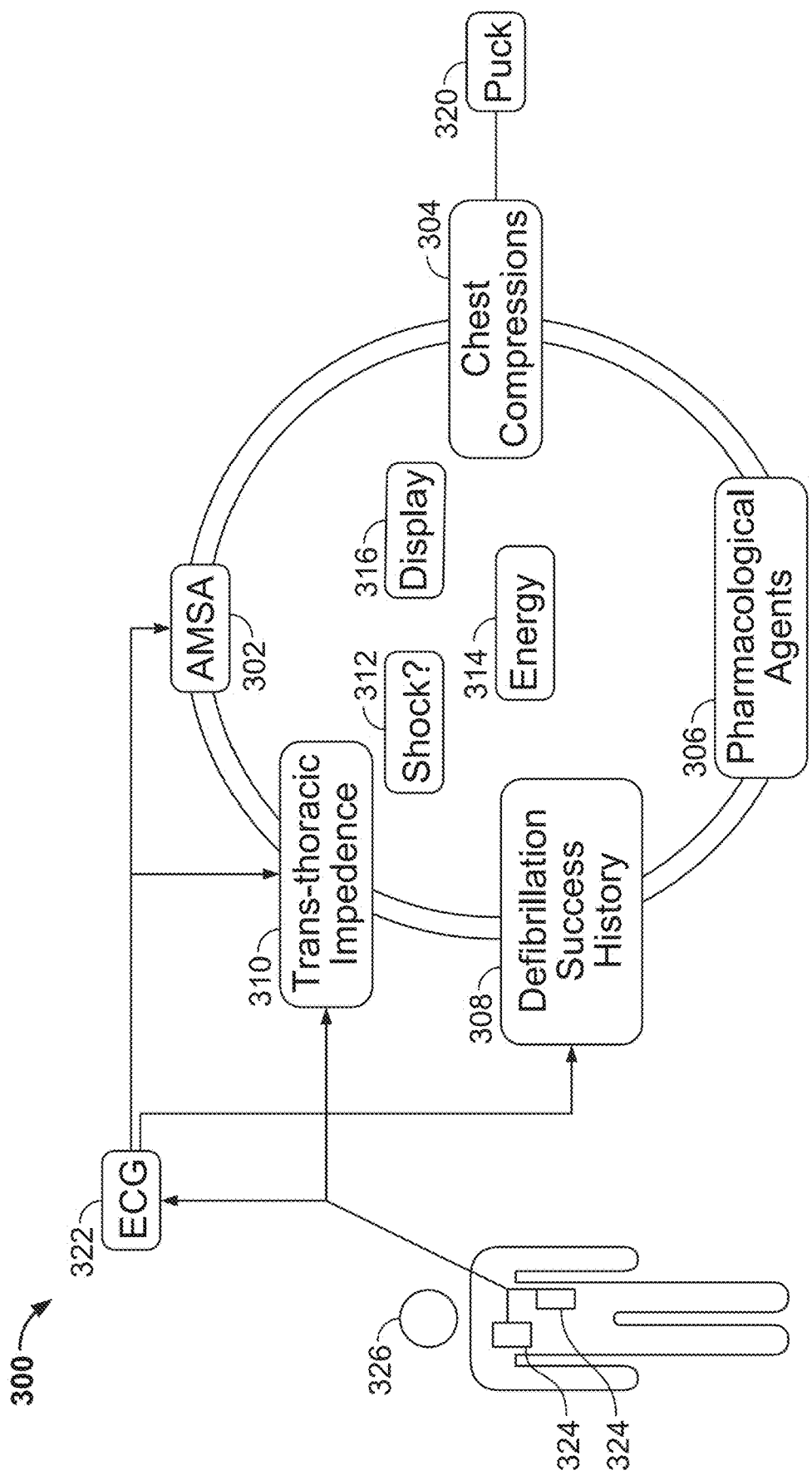
FIG. 3 shows consideration by a system of multiple signals in making shock determinations and recommendations.

FIG. 3 shows consideration by a system of multiple signals in making shock determinations and recommendations. As shown conceptually here, various input signals for determining a likelihood that a shock will be successful and for determining a best energy level for the shock are shown in a circle around the outputs that such signals may impact. In a particular implementation, one of the signals may be used alone, or multiple of the signals may be combined so as to create a composite energy or likelihood—e.g., by giving a score to each type and a weight, and combining them all to generate a weighted composite score for a likelihood.

The relevant signals may be generated from inputs that may obtain at least some of their data from signals generated by a pair of electrodes 324 that may be adhered to a patient's torso—above one breast and below the other, respectively, for example, in a typical manner. The electrodes may include leads for obtaining ECG data (e.g., via a 12-lead arrangement) and providing such data for analysis for a number of purposes. In addition, a CPR puck 320 may be placed on a patient's sternum and may deliver signals indicative of acceleration of the puck, and thus of up-down acceleration of the patient's sternum, which may be mathematically integrated so as to identify a depth of compression (and presence or absence of complete release) by the rescuer (and can also be used more simply to identify whether the patient is currently receiving chest compressions or not).

The electrodes 324 may be electrically connected to an ECG unit 322, which may be part of a portable defibrillator and may combine data from different leads (e.g., 8 or 12 leads) in a familiar manner to construct a signal that is representative of the patient's 326 ECG pattern. The ECG combination may also be represented mathematically as a vector value, such as including vector components in an XYZ representation. Such an ECG signal is often used to generate a visual representation of the patient's 326 ECG pattern on a screen of the defibrillator. The ECG-related data may also be analyzed in various ways to learn about the current condition of the patient 326, including in determining what sort of shock indication to provide in order to control the defibrillator or to display to a rescuer.

As one such example, ECG data may be provided to an AMSA analyzer 302, which may nearly continuously and repeatedly compute an AMSA number or similar indicator that represents ECG amplitude at particular different frequencies and/or frequency ranges in an aggregated form (e.g., a numeral that represents a value of the amplitude across the frequencies). The AMSA transform value may be determined from vectorized versions of the ECG readings so as to provide more predictive AMSA transform values. Similarly, power spectrum area can be measured and its value can be used as an input that is alternative to, or in addition to, an AMSA value for purposes of making a shock indication.

As described in more detail above and below, a current AMSA transform value (or a combination of multiple values over a short period taken in different windows of time) can be used to determine whether a shock is likely to be successful, and a plurality of combined AMSA transform values, such as a running average computed many times over a time period using a moving window may indicate how much time has elapsed since a cardiac event began and thus indicate which phase, of multiple phases during a VF event, the victim is in, where each phase calls for a different most-effective treatment sub-protocol. Also, when rescuers first arrive on a scene, several seconds of ECG data may be used to provide them an initial indication of the time since the event started and/or the phase in which the victim currently is in—e.g., by displaying a number of elapsed minutes or the name of one of multiple phases (like the three phases discussed above) on a display screen of a medical device such as a monitor or defibrillator/monitor.

The AMSA analyzer 302 may be programmed to perform the analysis on the ECG inputs, and perhaps other inputs, so as to maximize the predictive value of the AMSA readings, whether by affecting inputs to the AMSA determination, and/or making an AMSA determination and then adjusting the AMSA transform value that is generated from that determination. As one example, the size of the window in time from which ECG data is taken in making the calculation may be set to maximize the predictive value, such as by being about 1 second to about 1.5 seconds long. As another example, the shape of the window may be tapered, such as by being in the form of a Tukey or Hann window, rather than having vertical edges like a boxcar window. Similarly, the coefficients for the window, such as Chi$^2$ and p may be set to maximize the expected predictive value of the calculation.

The AMSA analyzer 302 may also be programmed to change such parameter values dynamically over the course of a particular VF incident, either by moving the values progressively as time elapses so as to make the values match known expected values for maximizing the predictive effect of the calculation, or to respond to particular readings, e.g., to use particular window length, form, or coefficients when an AMSA transform value is in a certain defined range.

The predictive quality of the AMSA determination may also be increased by performing the FFT or other transform in making the calculation on a vector value rather than a scalar value from the leads. Such an approach may provide a more complete picture of the operation of the heart, such as by catching minimums and maximums in the various signals more reliably and in capturing a picture of a greater portion of the heart rather than a particular point on the heart, where such point might be less representative of the overall condition of the heart. The overall process may thus better represent the actual condition of the heart, rather the non-indicative random changes in the signals.

The combination of ECG data from different leads may also be represented as a vector value in a three dimensional space. Such representations are termed "Vectorcardiography" (VCG), and represents the electrical activity of the heart as the motion of a vector in three dimensional space. Various lead systems, including, for example, the standard Frank XYZ lead system can be used for obtaining vectorcardiographic representations. The techniques described in this document can be adapted for data from such a Cartesian XYZ lead system by computing multidimensional discrete Fourier transforms (DFTs) on the data. In some implementations, fast Fourier transform (FFT) processes can be used in computing the multidimensional DFTs.

A multidimensional DFT is represented as:

$$X_k = \sum_{n=0}^{N-1} e^{-2\pi i k \cdot (n/N)} x_n$$

Therefore, the multidimensional DFT transforms an array $x_n$ with a d-dimensional vector of indices $n=(n_1, \ldots, n_d)$ by a set of d nested summations (over $n_j=0 \ldots N_j-1$ for each j), where the division n/N, defined as $n/N=(n_1/N_1, \ldots, n_d/N_d)$, is performed element-wise. The multidimensional DFT is therefore a composition of a sequence of d sets of one-dimensional DFTs, performed along one dimension at a time. The order in which the individual one dimensional DFTs are performed does not affect the results of the computation. Therefore, a multi-dimensional DFT can be computed, for example, using a row-column process, by performing a sequence of one-dimensional FFTs along one dimension (e.g., row-wise), followed by a sequence of one-dimensional FFTs along another dimension (e.g., column-wise). In some implementations, the column-wise FFTs can precede the row wise FFTs. This process can be extended for more than two dimensions for higher-dimension data.

In some implementations, the VCG may be described using a spherical coordinate system. For example, the spherical coordinates (r, θ, φ) can be used to represent radial distance r, polar angle θ (theta), and azimuthal angle φ (phi). The symbol ρ (rho) is often used instead of r. In some cases, Cartesian coordinate systems may not represent the activity of the electrical vector of the heart with sufficient resolution. However, because the activity is rotational in nature (with respect to a fixed origin), representing the VCG using a polar or spherical coordinate system may be of benefit in such cases.

In some implementations, because electrical activity is often impacted by the physical structure of the heart itself, it may be beneficial to align the spherical coordinate system with the physical structure of the heart. This can be accomplished, for example, by imaging of the heart at the time of VCG acquisition. By using a portable ultrasound system, such as the NanoMaxx with P21N probe (by Sonosite of Bothel Wash.), the location of the heart's apex, along with the angular axis of the heart can be determined. In some implementations, an inertial sensor system, such as the Analog Devices ADIS164362 Tri-Axis Gyroscope, Accelerometer, may be used to determine the position and angle of the ultrasound probe with respect to the location of the VCG apex electrode. The relative locations and angles of the heart's axis and apex position with respect to the VCG electrode can be stored along with the VCG. In some implementations, a rotational transform may align the zero polar and azimuthal angles of the spherical coordinate system of the VCG with the physical axis of the heart.

In some implementations, for example, when the VCG is represented in a spherical coordinate system, a Spherical Fourier Transform can be used as the transform. Examples of Spherical Fourier Transforms are described by Wang, et al., in "*Rotational Invariance Based on Fourier Analysis in Polar and Spherical Coordinates*," IEEE Transactions on Pattern Analysis and Machine Intelligence, VOL. 31, NO. 9, September 2009, and in Wang et al., "*Fourier Analysis in Polar and Spherical Coordinates*," Internal Report, Albert-Ludwigs University Freiburg, 2008. Spherical Fourier analysis can be defined as the decomposition of a function in terms of eigenfunctions of the Laplacian with the eigenfunctions being separable in the corresponding coordinates. The VCG can therefore be decomposed into wave-like basic patterns that have clear radial and angular structures. In some implementations, this decomposition can be an extension of Fourier analysis and can, therefore, be called Fourier analysis in the corresponding coordinates. In some cases, the radius of the VCG vector may undergo very little change, and the relevant changes occur primarily in the rotational dynamics of the heart's electrical vector. In such cases, using conventional Cartesian spectral analysis can cause the rotational dynamics to be inadequately represented by the rectangular representation.

In some implementations, determining a likelihood of success from delivering a future defibrillating shock can comprise performing a mathematical transform on the ECG data. The mathematical transform can be done using Fourier, discrete Fourier, Hilbert, discrete Hilbert, wavelet, and discrete wavelet methods. In some implementations, the determination of the likelihood of success can include a zero-crossing-based analysis, an example of which is described in Kedem, *Spectral Analysis and Discrimination by Zero-Crossings*, Proceedings of the IEEE, Vol 74, No 11, November 1986. Zero-crossing counts in filtered time series may be referred to as higher order crossings. In addition, determining a likelihood of success from delivering a future defibrillating shock comprises performing a calculation by an operation, such as logistic regression, table look-up, neural network, and fuzzy logic.

A CPR chest compression module 304 provides another signal and may receive signals about the motion of the puck 320 to determine whether chest compressions are currently being applied to the patient, and to determine the depth of such compressions and whether full release is occurring. Such information may be used, for example, in giving a rescuer feedback about the pace and depth of the chest compressions (e.g., the defibrillator could generate a voice that says "push harder"). The presence of current chest compression activity may also signal the other components that a shock is not currently advisable, or that ECG data should be analyzed in a particular manner so as to remove residual artifacts in the ECG signal from the activity of the chest compressions.

Information about pharmacological agents 306 provided to a patient may also be identified and taken into account as another signal in providing a shock indication to a rescuer and selecting an energy level for any shock. Such information may be obtained manually, such as by a rescuer entering, via a screen on a defibrillator or on a tablet computer that communicates with the defibrillator, identifiers for the type of agent administered to a patient, the time of administration, and the amount administered. The information may also be obtained automatically, such as from instruments used to administer the particular pharmacological agents. The device that provides a shock indication may also take that information into account as yet another signal in identifying the likelihood that a shock will be successful if provided to the patient (e.g., by shifting up or down an AMSA threshold for measuring shock success likelihood), and for other relevant purposes such as determining an energy to apply in the shock.

A defibrillation history success module 308 tracks the application of defibrillating shocks to the patient and whether they were successful in defibrillating the patient, and/or the level to which they were successful. For example, the module 308 may monitor the ECG waveform in time windows of various sizes for a rhythm that matches a profile of a "normal" heart rhythm, and if the normal rhythm is determined to be established for a predetermined time period after the application of a defibrillating shock, the module 308 may register the existence of a successful defibrillating shock. If a shock is applied and a normal rhythm is not established within a time window after the delivery of the shock, the module 308 can register a failed shock. In addition to registering a binary value of success/fail, the module may further analyze the ECG signal to determine the level of the success or failure and may, for example, assign a score to the chance of success of each shock, such as a normalized score between 0 (no chance of success) and 1 (absolute certainty).

With respect to modifying an AMSA or other shock prediction algorithm (SPA) score, or affecting the manner in which such score is computed based on prior success or failure in delivering defibrillating shocks, it has been observed that victims of cardiac fibrillation will successfully defibrillate for lower AMSA threshold values if they have been previously successfully defibrillated during the same rescue session. Such a determination may also be combined with determinations about trans-thoracic impedance (trans-thoracic impedance) of the patient, or other measured factors, as discussed more fully below.

Particular techniques discussed here, including selection of proper window size for the ECG data, proper window type, proper coefficients, and the use of vectorized operations in calculating the AMSA, may improve the quality of the AMSA scoring process. An AMSA score may also be used to determine where, time-wise, a person is in the process of suffering from cardiac arrest and fibrillation, since defibrillating shocks may be much less effective after a person has been fibrillating for several minutes, and CPR (including forceful CPR) may be a preferred mode of treatment instead. Such systems may also combine a current AMSA transform value (e.g., for recommending a shock) with a trend in AMSA transform value over time (e.g., for recommending chest compressions instead of a shock), where some or all of the AMSA transform values may be made from vector input.

A trans-thoracic impedance module 310 may also obtain information from sensors provided with the electrodes 324, which indicates the impedance of the patient between the locations of the two electrodes. The impedance can also be a factor in determining a shock indication, such as by taking into account an impedance in altering the AMSA score that will trigger a recommendation for providing a defibrillating shock. It would be understood that mathematically, such additional factors such as TTI may be used as inputs to an AMSA-related calculation, or may be used to modify a result of an AMSA-related calculation.

One or more of the particular factors or signals discussed here may then be fed to a shock indication module 312 and/or an energy selection module 314, which may combine them each according to an appropriate formula so as to generate a binary or analog shock indication and a proposed energy level for a shock, respectively. For example, any of the following appropriate steps may be taken: a score may be generated for each of the factors, the scores may normalized (e.g., to a 0 to 1 or 0 to 300 scale), a weighting may be applied to each of the scores to represent a determined relevance of that factor to the predictability of a shock outcome or energy level to be delivered, the scores may be totaled or otherwise combined, and an indication can be determined such as a go/no go indication, a percentage of likely success, and other such indications.

The results of such determinations may also be provided to a display module 316, which may generate a presentation to be provided to a rescuer who is operating the defibrillator. Such presentation, may be visual, auditory, haptic, or a combination of the three. For example, if a shock is determined to be likely to succeed if it is provided, the display module 316 may cause a screen on the defibrillator to display a binary indication such as "Ready to deliver shock" or an analog indication such as "80% likelihood of successful shock." Similarly, the display module may cause a screen to show a message such as "200 J" One or more of these message may alternatively or additionally be spoken by computer-generated voice into a speaker on the defibrillator or into a wireless earpiece worn by a rescuer or rescuers.

In this manner then, the system 300 may take into account one or a plurality of factors and treat them as input signals in determining whether a shock to be delivered to a patient is likely to be successful. The factors may take data measured from a plurality of different inputs (e.g., ECG, TTI, delivered agents, etc.), and may be combined to create a likelihood indication, such as a numerical score that is to be measured against a predetermined scale (e.g., 0 to 300% likelihood or A to F grade). They may also be used to select an appropriate energy level for delivery of a shock. In some implementations, different ones of the factors may be used in the likelihood of success determination than in the energy level determination. Additional determinations may also be made with one or more of the signals. Such determinations may then be used to control an automatically-operated system (e.g., that delivers chest compressions mechanically), to limit operation of a manually-operated system (e.g., by enabling a shock that is triggered by a user pressing a button), or by simply providing information to a system whose shock is determined solely by a rescuer (e.g., for manual defibrillators in which the operator is a well-trained professional, or a hybrid defibrillator that is set in a manual mode).

Figure 4:
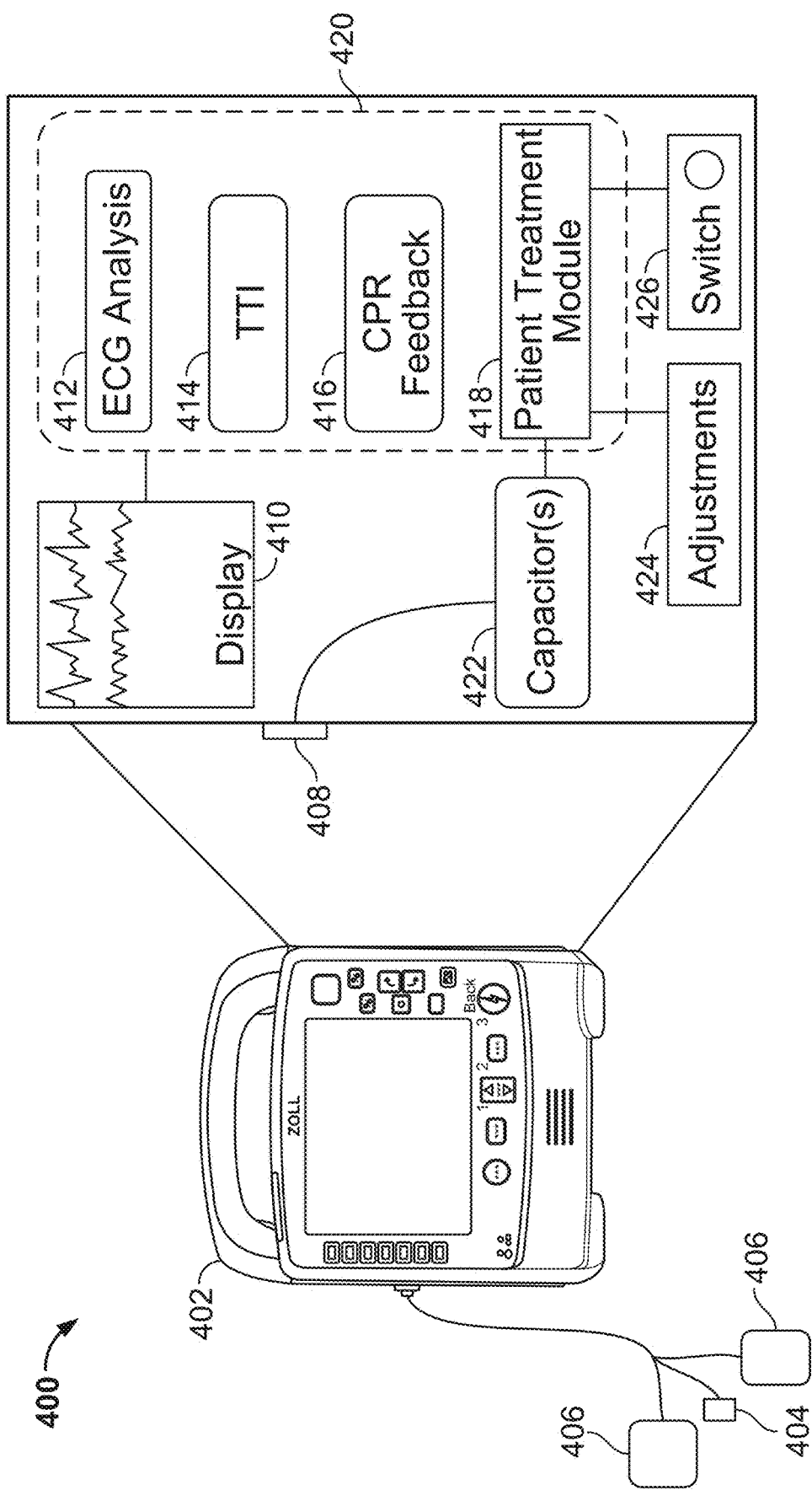
FIG. 4 is a schematic diagram of a portable defibrillator.

FIG. 4 is a schematic diagram of a portable defibrillator system 400. In this example, defibrillator 402, along with an example electrode package 406 and compression puck 404, defines an apparatus for administering care to a patient who requires cardiac assistance (where the term patient addresses any human individual in need of assistance, and is not limited to someone who has been checked into a healthcare system already). Other components (not pictured) may also be provided, including in-ambulance and in-hospital display systems that can wirelessly communicate with the defibrillator 402 and display information received from the defibrillator 402; and wearable computing devices, such as electronic glasses that provide visual annotations on a scene that a user views, which may be worn by rescuers and provide critical information about a patient visually or aurally, including each of the types of information discussed here and with respect to FIG. 6 below.

Particular components of the defibrillator 402 are shown here to indicate certain particular functionality provided by the defibrillator 402, though additional features that are not shown may also be provided. For example, defibrillator 402 includes a switch 426 and at least one capacitor 422 for selectively supplying or applying a shock to a patient. The defibrillator 402 further includes an ECG analyzer module 412, a trans-thoracic impedance module 414, a CPR feedback module 416 that controls frequency and magnitude of chest compressions applied to a subject, a patient treatment (PT) module 418 (which includes a defibrillation history analyzer), a speaker, and a display 410.

In this example, the ECG analyzer module 412, trans-thoracic impedance module 414, CPR feedback module 416, and patient treatment (PT) module 418 are grouped together as a logical module 420, which may be implemented by one or more computer processors executing software stored on one or more non-transient recordable media. For example, respective elements of the logical module 420 can be implemented as: (i) a sequence of computer implemented instructions executing on at least one computer processor of the defibrillator 402; and (ii) interconnected logic or hardware modules within the defibrillator 402.

In the example of FIG. 4, the electrode package 406 is connected to the switch 426 via port 408 on the defibrillator 402 so that different packages may be connected at different times (e.g., if a customer wants to buy different model numbers of packages, or if the customer wants to replace a disposable package that has been used or otherwise become ineffective). The electrode package 406 may also be connected through the port 408 to ECG analysis module 412, and TTI module 414, and may include A/D conversion before being provided to the logical module 420. The electrode package 406 includes electrodes for delivering a defibrillating electrical pulse to a patient in addition to capturing electrical signals from the heart that indicate ECG functioning. In this example, there are a plurality of physical and signal (pairs of physical) leads so that vector representations of the ECG data may be collected and processed—e.g., to developed a vectorized AMSA reading for the patient from the ECG data.

The compression puck 404 is connected, in this example, to the CPR feedback module 416, also via port 408. In one embodiment, the ECG analysis module 412 is a component that receives ECG signals and produces a digital ECG representation form the signals, where the produced ECG representation represents a current streaming ECG representation capable of analysis and display in familiar manners. Similarly, the TTI module 414 is a component that receives TTI data that represents a current impedance across a patient's torso where the electrodes 406 have been placed.

The patient treatment module 418 is configured to receive an input from each one of the ECG analyzer module 412, TTI module 414, and CPR feedback module 416. The patient treatment module 418 uses inputs as received from at least the ECG analyzer module 412 and trans-thoracic impedance module 414 to predict whether a defibrillation event will likely terminate an arrhythmic episode, and to identify an energy level (or at least a presumptive energy level that can be overrideen by an expert user) at which the shock will be delivered. For example, ECG data can be used both to determine AMSA transform values for a patient (including via vectorized methods), and also determine whether shocks are effective or not so that such information can be saved and used to identify likelihoods that subsequent shocks will be effective. In this manner, the patient treatment module 418 uses information derived from both an ECG signal (both for AMSA and for adjusting the AMSA value) and TTI measurement to provide a determination of a likelihood of success for delivering a defibrillating shock to a subject, and for selecting an energy level.

The patient treatment module 418 is further configured to provide an input to each one of the speaker, display 410, and switch 426, either directly or indirectly. In general, input provided to the speaker and display 410 corresponds to either a success indication or a failure indication regarding the likelihood of success for delivering a shock to the patient, and display or other presentation of an energy level at which the shock will be delivered. In one embodiment, the difference between a success indication and a failure indication is binary and based on a threshold. For example, a success indication may be relayed to the display 410 when the chances corresponding to a successful defibrillation event is greater than 75%, and a "no shock" indication when it is less then 75% (accompanied potentially by a lock-out of the ability to deliver a shock with the defibrillator 402). In such example, the value "75%" (or some higher value) may be rendered on the display 410 indicating a positive likelihood of success. When a positive likelihood of success is indicated, the patient treatment module 418 enables the switch 426 such that a shock may be delivered to a subject.

The patient treatment module 418 may also implement an ECG analyzer for generating an indication of heart rate for the patent, for generating an indication of heart rate variability for the patent, an indication of ECG amplitude for the patent, and/or an indication of a first or second derivative of ECG amplitude for the patient. The indication of ECG amplitude can include an RMS measurement, measured peak-to-peak, peak-to-trough, or an average of peak-to-peak or peak-to-trough over a specified interval. Such indications obtained by the ECG analyzer may be provided to compute an AMSA transform value for the patient and/or can be used in combination with a computed AMSA transform value so as to generate some derivative indication regarding whether a subsequent shock is likely or unlikely to be effective (and the degree, e.g., along a percentage scale, of the likelihood).

In another embodiment, likelihood of a successful defibrillation event may be classified into one of many possible groups such as, for example, low, medium, and high likelihood of success. With a "low" likelihood of success (e.g., corresponding to a successful defibrillation event is less than 50%), the patient treatment module 418 disables the switch 426 such that a shock cannot be delivered to a subject. With a "medium" likelihood of success (e.g., corresponding to a successful defibrillation event is greater than 50% but less than 75%), the patient treatment module 418 enables the switch 426 such that a shock may be delivered to a subject, but also renders a warning on the display 410 that the likelihood of success is questionable. With a "high" likelihood of success (e.g., corresponding to a successful defibrillation event is greater than or equal to 75%), the patient treatment module 418 enables the switch 426 such that a shock may be delivered to a subject, and also renders a cue on the display 410 indicating that the likelihood of success is very good. Still other embodiments are possible.

Thus, the system 400 may provide, in a portable electric device (e.g., a battery-operated device) the capability to analyze a number of inputs and to identify a variety of factors from those inputs, where the factors can then be combined to provide a flexible, intelligent determination of likely success. As one such example, an energy to be delivered (as a set value or a default value that can be overridden).

Figure 5:
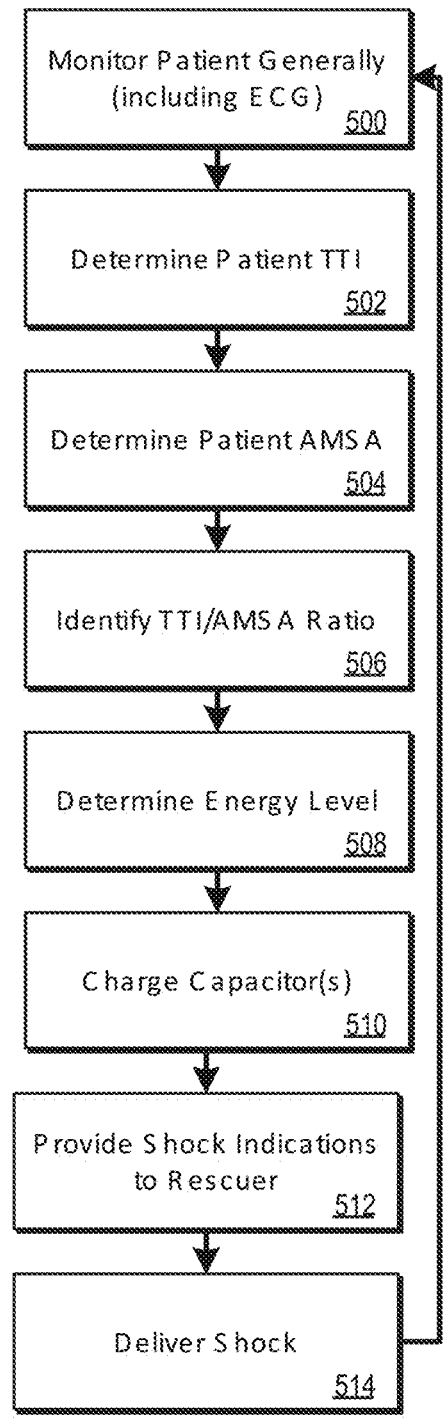
FIG. 5 is a flow chart of a process for determining an energy level for a defibrillator.

FIG. 5 is a flow chart of a process for determining an energy level for a defibrillator. In general, the process involves collecting data from a patient who is being treated by rescuers and using that data to identify an appropriate energy level to deliver in a future shock to the patient, if it is determined that the patient is in need of and susceptible to a defibrillating shock. In particular, the data may include ECG data collected from electrodes placed on the patient, and converted using a shock prediction algorithm such as amps up. The process may be carried out using the structures shown in FIGS. 3 and 4 above, and including use of the patient treatment module 418 for determining energy levels for delivery of a shock or shocks to a patient.

The process begins at box 500, where a patient is generally monitored by a medical device such as a portable defibrillator at the site of a rescue attempt. The monitoring may occur subsequent to rescuers attaching electrodes to a patient, where the electrodes may be configured both to provide a defibrillating shock and also to collect lead information for generating ECG data. The monitoring may occur substantially continuously, in a typical manner, and data from the monitoring may be displayed on the medical device, such as by displaying a continuous readout of the patient's pulse, ECG, blood pressure, and other relevant medical information.

At box 502, a TTI for the patient is determined. Such determination may be made by providing a small electric current between the electrodes have been applied to the patient, measuring voltage across the electrodes, and determining impedance by way of homes law.

At box 504, the patient's AMSA is determined. Such determination may occur, for example, by applying a fast Fourier transfer (FFT) to multiple dimensions of the ECG data, and forming an AMSA transform value out of such vectorized ECG data. Thus, the transformations may occur via the use of vectorized FFTs applied to vectors formed by different leads that have collected the ECG data, The value may also, in addition to or alternatively to, being an AMSA transform value, be a value computed from ECG data, including amplitude data of an ECG representation, to determine a shock success prediction level.

Rather than treating each shock as a discrete event in analyzing the probability of success, the techniques described here can take into account prior shock deliveries, and an observed response of the patient to those deliveries, in determining an AMSA transform value or other value that will indicate that a shock currently applied to the patient will likely be successful (or not) in defibrillating the patient. Such a determination may also be combined with determinations about trans-thoracic impedance (trans-thoracic impedance) of the patient, or other measured factors, as discussed more fully below.

To obtain better predictive value for the AMSA transform values, the time window from which the ECG data for an AMSA determination is taken may be made relative small (e.g., between 3 and 4 seconds, between 2 and 3 seconds, and between 1 and 2 seconds), which will place the data as close to the current status of the patient as possible. Smaller windows may suffer from edge effects more-so than would larger windows, so the shape (e.g., a tapered window) and coefficients for the windows may also be selected to maximize predictive power of the method. For example, a Tukey window having appropriate coefficients may be employed, and the measurements may be made across multiple scalar lead values with the data being processed as a vector representation of those scalar values.

The techniques discussed here receive input from a plurality of ECG leads (e.g., from a 12-lead system) and characterize that input as a vector value, where the vector that may be made up of three orthogonal (X, Y, and Z) vectors from the plurality of leads and can be understood as rotating through a complex space with each cycle of a heartbeat. A complex FFT operation may then be conducted on the vector representation in order to compute a vectorized amplitude spectrum area (AMSA) transform value, where the AMSA transform value is a numerical value that is based on the sum of the magnitude of a weighted frequency distribution from the signal, e.g., between 3 and 48 Hz. Generally, the greater the AMSA, the greater the probability that an applied shock will defibrillate the heart successfully.

The particular parameters for computing the vectorized AMSA value may be selected so as to maximize the predictive capabilities of a medical device. For example, a tapering function may be applied to the ECG data window (e.g., by using a Tukey window), so as to improve the accuracy of the FFT applied to the data. Such a tapered window may prevent the data from jumping immediately from a zero value up the measured values, and then back down immediately to a zero value at the end of a measured window. Various parameters for the tapering function may also be applied, such as coefficients to define the slopes of the starting and ending edges of the function. Moreover, the length of the window may be selected to provide better data, such as by using a relatively short window having a duration shorter than 4 seconds, and in certain examples of about 1 second, between 1 and 2 seconds, between 1 and 3 seconds, between 2 and 3 seconds, or between 3 and 4 seconds long.

In certain other implementations, multiple different tapering functions may be applied to the same data essentially simultaneously, AMSA transform values may be determined from each such applied function, and the resulting AMSA transform value from one of the functions may be selected, or an AMSA transform value may be generated that is a composite from multiple different tapering functions. The window function that is used, the length of the window, and the coefficients for the window may also be adjusted dynamically, so that one or more of them change during a particular incident, or deployment, with a particular patient. For example, it may be determined from analysis of prior data that a certain window shape, size, and/or coefficients are better earlier in an episode of VF than later, so that a defibrillator may be programmed to change such parameters over the course of an event.

Such changes may be tied to an initial determination about how long the patient has been in VF, which may be a function of user input (e.g., when the emergency call was made) and parameters measured by the defibrillator. Also, changes to the window type, size, and coefficients may be made from readings dynamically made from the patient under treatment. For example, AMSA transform values in a particular range may be measured better by a particular window type, size, or range of coefficients, so that an AMSA measurement made at time n that shows such a value, may be measured using the other parameters known to work best with that AMSA transform value at time n+1. Other techniques for dynamically adjusting the window type, window size, and/or coefficients may also be employed.

With respect to indications of where a victim is in the process of a VF episode—e.g., how many minutes since the victim's episode has started—an average AMSA transform value (including as a vectorized AMSA transform value) may be determined over a time period so as to identify more generalized changes in the victim's AMSA transform values, rather than AMSA at a particular point in time or small slice of time. For example, AMSA transform values can be computed for particular points in time or particular windows in time and those values can be saved (e.g., in memory of a patient monitor or defibrillator). After multiple such measurements and computations have been made, an average may be computed across multiple such values. Because AMSA generally falls (on average) over time in an episode, if the average for a certain number of readings (e.g., a moving average) falls below a particular value or falls below the value over a minimum time period (so as to indicate the general AMSA condition of the victim rather than just a transient reading), the device may provide additional feedback to a rescuer.

These general phases of cardiac arrest or VF may be identified, in one representation, as three separate phases (though there may be some overlap at the edges of the phases): electrical, circulatory, and metabolic. The electrical phase is the first several minutes of an event, and marks a period during which electric shock can be particularly effective in defibrillating the victim's heart and returning the victim to a relative satisfactory condition. The circulatory phase appears to mark a decrease in effectiveness for electric shock in defibrillating the victim, and particularly in the absence of chest compressions performed on the victim. As a result, a device such as a portable defibrillator may be programmed to stop advising shocks during such a phase (or may advise a shock only when other determinations indicate that a shock would be particularly likely to be effective) and may instead advise forceful CPR chest compressions. Such forceful compressions may maximize blood flow through the heart tissue and other parts of the body so as to extend the time that the victim may survive without lasting or substantial damage.

In the metabolic phase, chest compressions may be relatively ineffective as compared to the circulatory phase. For example, where tissue has become ischemic, such as in circulatory phase, the tissue may react favorably to the circulation of blood containing some oxygen, but where tissue has become severely ischemic, such as in the metabolic phase, the introduction of too much oxygen may be harmful to the tissue. As a result, more gentle compressions for the first period, such as 30 seconds, may need to be advised in the metabolic phase before the rescuer (or a mechanical chest compressor controlled to provide appropriate levels of compression following the points addressed here) uses a full force.

Other treatments that may be useful in the metabolic phase include extracorporeal circulation and cooling, either alone, in combination with each other, or in combination with other pharmacological treatments. In any event, observation of elapsed time since an event has begun and/or observation of the phase in which a victim is in, may be used to control a device or instruct a rescuer to switch from a first mode of providing care to a second mode of providing care in which the parameters of the provided care differ (e.g., speed or depth of chest compressions may change, temperature-based therapy may be provided or stopped, or pharmaceuticals may be administered).

At box 506, a ratio of the TTI to AMSA is determined. The ratio may be simple, such as by simply dividing the actual TTI value by the AMSA transform value. The ratio may alternatively, or in addition, be generated based on normalized values for TTI and for AMSA, so as to provide a ratio that is more easily handled by additional steps of the process. For example, the input values may be scaled, so as to provide a linear output value for the ratio.

At box 508, an energy level for a shock to be delivered is determined. Such determination may occur by applying a value from a shock prediction algorithm, such as an AMSA transform value, to a predefined formula, to a lookup table, or by way of other mechanisms for determining an energy level to supply. In other implementations, a ratio between the TTI value and the AMSA transform value may be used in a similar manner (e.g., by applying it to a formula, look-up, etc.). The determination may also take into account other variables, either as part of combining those variables with the AMSA and TTI values, or by applying corrections after an initial determination is made using AMSA, TTI, or both.

At box 510, the capacitor or multiple capacitors in a defibrillator may be charged to the determined energy level. Such charging may occur automatically and at this point in the process, or may occur at a later point in the process, such as after a rescuer has indicated that they would like to provide a shock. Also, the computed energy level and charging of capacitors may, in certain circumstances, occur only after the process has determined that the patient has a shockable heart rhythm, so that a shock is advised at all. The determination of a shockable heart rhythm may be part of determining a likelihood of success for applying a shock or may be separate from such a determination. For example, the determination of a shockable rhythm may be a threshold step before making further calculations and may be a relative simple determination to make. In contrast, the determination of a likelihood of success may be more complex and may occur after a shock a bowl rhythm is determined.

At box 512, shock indications are provided to the rescuer. Such indications may include the energy level that has been computed by the device as well as an indication of a likelihood of a shock that is currently delivered being a success in defibrillating the patient. Such presentation, as indicated above and below, may include displaying a percentage likelihood of the shock succeeding, displaying a letter grade, or displaying a binary indication that a shock is or is not currently advised. The presentation may also be audible or haptic. In certain implementations, especially where the defibrillator is a manual or professional defibrillator, or when the defibrillator is in a manual mode, the computed energy may be overridden by the rescuer, as may the determination of whether a shock is or is not currently advisable, though the system may place a lower limit on a likelihood of success even for manual mode, so that if the likelihood is below that limit, even a skilled operator cannot override the determination to not deliver a shock.

Additional information provided to a rescuer may take the form of instructions, such as instructions to perform chest compressions or some other action, where the action is selected from among a plurality of possible treatments based on the current phase for the victim. A system may also integrate both automatic and manual approaches—e.g., locking out the ability to provide a shock until a threshold level is reached, and then showing the relative likelihood of success above that value. The likelihood of success can be shown in various manners, such as by showing an actual percentage, or showing two or more of a low, medium, or high likelihood of success, e.g., on an electronic display of a defibrillator.

At box 514, the process delivers the shock to the patient. In such a situation, the information may have been provided to the rescuer and the delivery of a shock enabled because the information indicated that the likelihood of success was sufficient. In response, the rescuer may have pushed a shock button to deliver the shock, the device have waited a sufficient time for the rescuer to remove his hand from the device, and then the device having closed a switch automatically between the capacitors and the patient so as to deliver the stored energy from the capacitors to the patient at a level (e.g., in Joules) that was determined by the device or entered by the rescuer. In certain implementations, the capacitor may be pre-charged to a level that does not match the level determined by the device or entered by a user when the shock is going to be provided. In such circumstances, additional charge may be provided to the capacitors or charge may be released from the capacitors before delivering the shock, so that the energy level that is determined or selected may be the appropriate energy level delivered to the patient.

In this manner, the process allows a medical device such as a defibrillator to deliver a shock at the time that is most appropriate and most likely to defibrillator a patient, and any energy level that is most likely to defibrillator the patient. As a result, the patient may be more likely to be defibrillator from the shock, and to be defibrillator with fewer shocks and plus less damage from failed shocks.

Figure 6:
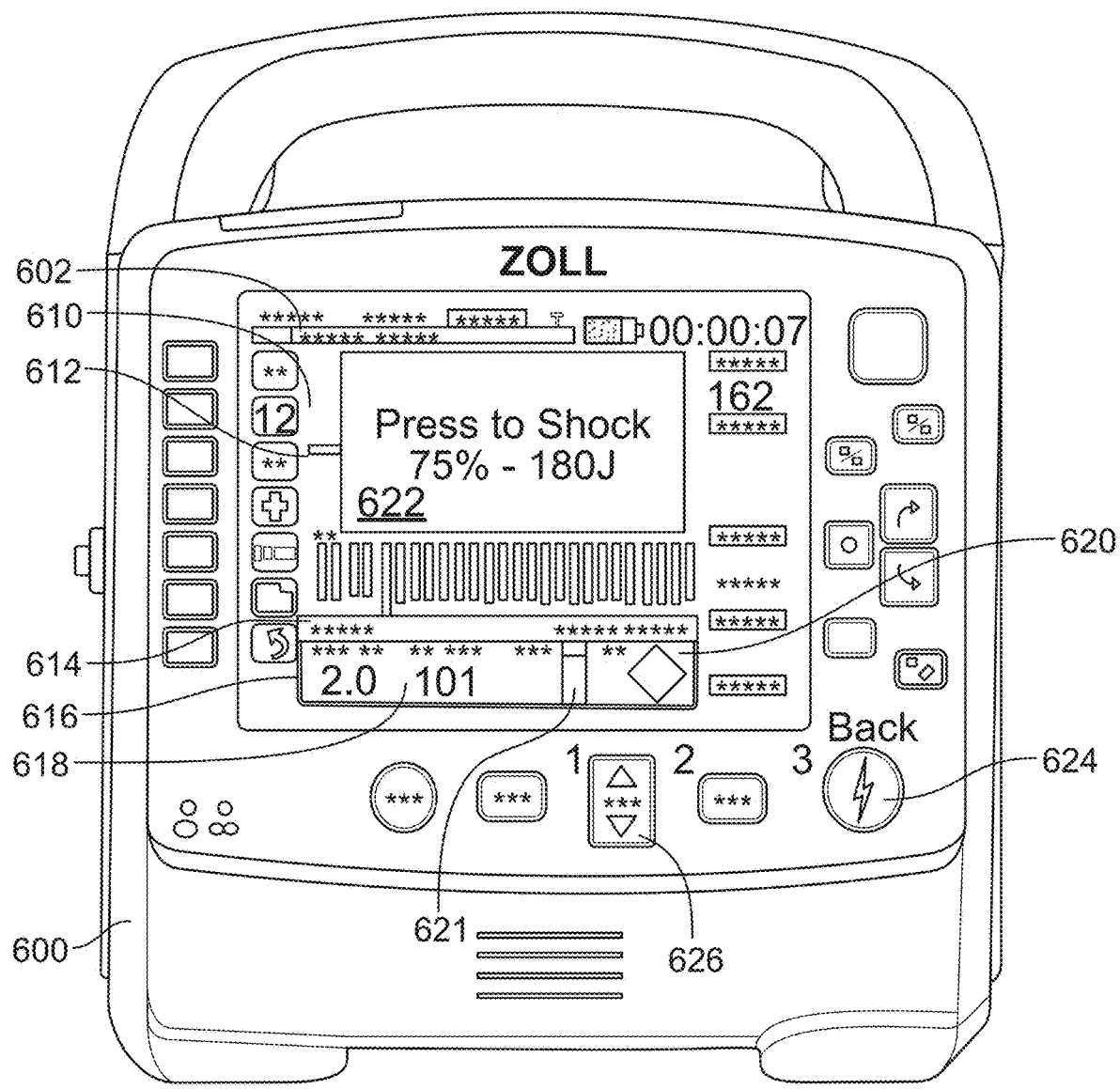
FIG. 6 shows a defibrillator showing certain types of information that can be displayed to a rescuer.

FIG. 6 shows a defibrillator showing certain types of information that can be displayed to a rescuer. In the figure, a defibrillation device 600 with a display portion 602 provides information about patient status and CPR administration quality during the use of the defibrillator device. As shown on display 602, during the administration of chest compressions, the device 600 displays information about the chest compressions in a box on the same display 602 as is displayed a filtered ECG waveform 610 and a CO2 waveform 612 (alternatively, an SpO2 waveform can be displayed). The device 602 may be an implementation of the defibrillator 402 shown schematically in FIG. 4 or similar forms of devices. The presentation here is intended to show an example of a typical device layout and information that can be presented to a user of the device 600.

During chest compressions, the ECG waveform 610 is generated by gathering ECG data points and accelerometer readings, and filtering the motion-induced (e.g., CPR-induced) noise out of the ECG waveform. Measurement of velocity or acceleration of chest compression during chest compressions can be performed according to the techniques taught by U.S. Pat. No. 7,220,335, titled "Method and Apparatus for Enhancement of Chest Compressions During Chest Compressions," the contents of which are hereby incorporated by reference in its entirety.

Displaying the filtered ECG waveform helps a rescuer reduce interruptions in CPR because the displayed waveform is easier for the rescuer to decipher. If the ECG waveform is not filtered, artifacts from manual chest compressions can make it difficult to discern the presence of an organized heart rhythm unless compressions are halted. Filtering out these artifacts can allow rescuers to view the underlying rhythm without stopping chest compressions.

Box 614 shows a rescuer information about the manner in which they are and recently have been performing chest compressions on the patient. The CPR information in box 614 is automatically displayed when compressions are detected by the device 600. The information about the chest compressions that is displayed in box 614 includes rate 618 (e.g., number of compressions per minute) and depth 616 (e.g., depth of compressions in inches or millimeters). The rate and depth of compressions can be determined by analyzing accelerometer readings, e.g., mounted in a puck placed on a sternum of the patient. Displaying the actual rate and depth data (in addition to, or instead of, an indication of whether the values are within or outside of an acceptable range) can also provide useful feedback to the rescuer. For example, if an acceptable range for chest compression depth is 1.5 to 2 inches, providing the rescuer with an indication that his/her compressions are only 0.5 inches can allow the rescuer to determine how to correctly modify his/her administration of the chest compressions (e.g., he or she can know how much to increase effort, and not merely that effort should be increased some unknown amount).

A perfusion performance indicator (PPI) 620 is also displayed to provide feedback to a rescuer or rescuers to help them improve their performance with respect to the patient. The PPI 620 is displayed here as a shape (e.g., a diamond) with the amount of fill that is in the shape (from 0 to 100%) differing over time to provide feedback about both the rate and depth of the compressions. When CPR is being performed adequately, for example, at a rate of about 100 compressions per minute (CPM) with the depth of each compression greater than 1.5 inches, the entire indicator will be filled. As the rate and/or depth decreases below acceptable limits, the amount of fill lessens. The PPI 620 provides a visual indication of the quality of the CPR such that the rescuer can aim to keep the PPI 620 completely filled.

The data displayed to the rescuer can change based on the actions of the rescuer or rescue team. For example, the data displayed can change based on whether the rescuer is currently administering CPR chest compressions to the patient. Additionally, the ECG data 610 displayed to the user can change based on the detection of CPR chest compressions. For example, an adaptive filter can automatically turn on or off based on detection of whether CPR is currently being performed. When the filter is on (during chest compressions), the filtered ECG data is displayed and when the filter is off (during periods when chest compressions are not being administered), unfiltered ECG data is displayed. An indication of whether the filtered or unfiltered ECG data is displayed can be included visually with the waveform (e.g., via an indicative icon).

The display also shows a reminder 621 regarding "release" in performing chest compression. Specifically, a fatigued rescuer may begin leaning forward on the chest of a victim and not release pressure on the sternum of the victim at the top of each compression. This can reduce the perfusion and circulation accomplished by the chest compressions. The reminder 621 can be displayed when the system recognizes that release is not being achieved (e.g., signals from an accelerometer show an "end" to the compression cycle that is flat and thus indicates that the rescuer is staying on the sternum to an unnecessary degree). Such a reminder can be coordinated with other feedback as well, and can be presented in an appropriate manner to get the rescuer's attention. The visual indication may be accompanied by additional visual feedback near the rescuer's hands, and by a spoken or tonal audible feedback, including a sound that differs sufficiently from other audible feedback so that the rescuer will understand that release (or more specifically, lack of release) is the target of the feedback.

Box 622 shows an indication of a likelihood that a shock, if currently administered, will be effective in defibrillating the patient. Here, the likelihood is indicated as being 75%, which is above a threshold value, so the defibrillator 600 is recommending that the rescuer press a button 624 that will operate a switch to cause energy to be discharged into the patient. The likelihood determination may have been made by a process that takes in vector ECG values, and produces an AMSA transform value (repeatedly) for the patients using such data as it arrives on a plurality of leads that are connected to the patient via electrodes and to the defibrillator 600 wire one or more ports into which the physical ECG leads can be plugged in a familiar manner.

Box 622 also displays a value, in Joules, to indicate the energy that will be delivered by the shock if it is delivered. Such value may have been determined, as described above, using AMSA or other ECG-derived values, including values that look to a weighting of the ECG spectrum and/or that use transforms such as FFT's to make such determination conveniently and efficiently. Energy adjustment button 626 is a rocker button that allows the rescuer to adjust the energy up or down from the values that is displayed, and if the rescuer engages the button 626, box 622 may be updated, e.g., to show 5 more or less Joules, depending on whether the rescuer engaged the top or the bottom of the button 626, respectively.

FIG. 6's particular displays may be implemented, as noted above, with a system that uses particular techniques to improve the accuracy of a prediction that an applied shock will be a success and that uses AMSA or other SPA values in making such a prediction. For instance, the feedback provided by the displays in the figures can be determined by selecting an appropriate ECG window size for calculating AMSA on vectorized values (e.g., one second or slightly longer, such as 1.5 seconds or 2 seconds), a window type (e.g., Tukey), and particular coefficients for the window. Such factors can also be changed over the time of a VF event, as discussed above, so as to maintain a most accurate predictor of defibrillation success.

While at least some of the embodiments described above describe techniques and displays used during manual human-delivered chest compressions, similar techniques and displays can be used with automated chest compression devices such as the AUTOPULSE device manufactured by ZOLL Medical Corporation of Chelmsford, Mass.

Figure 7:
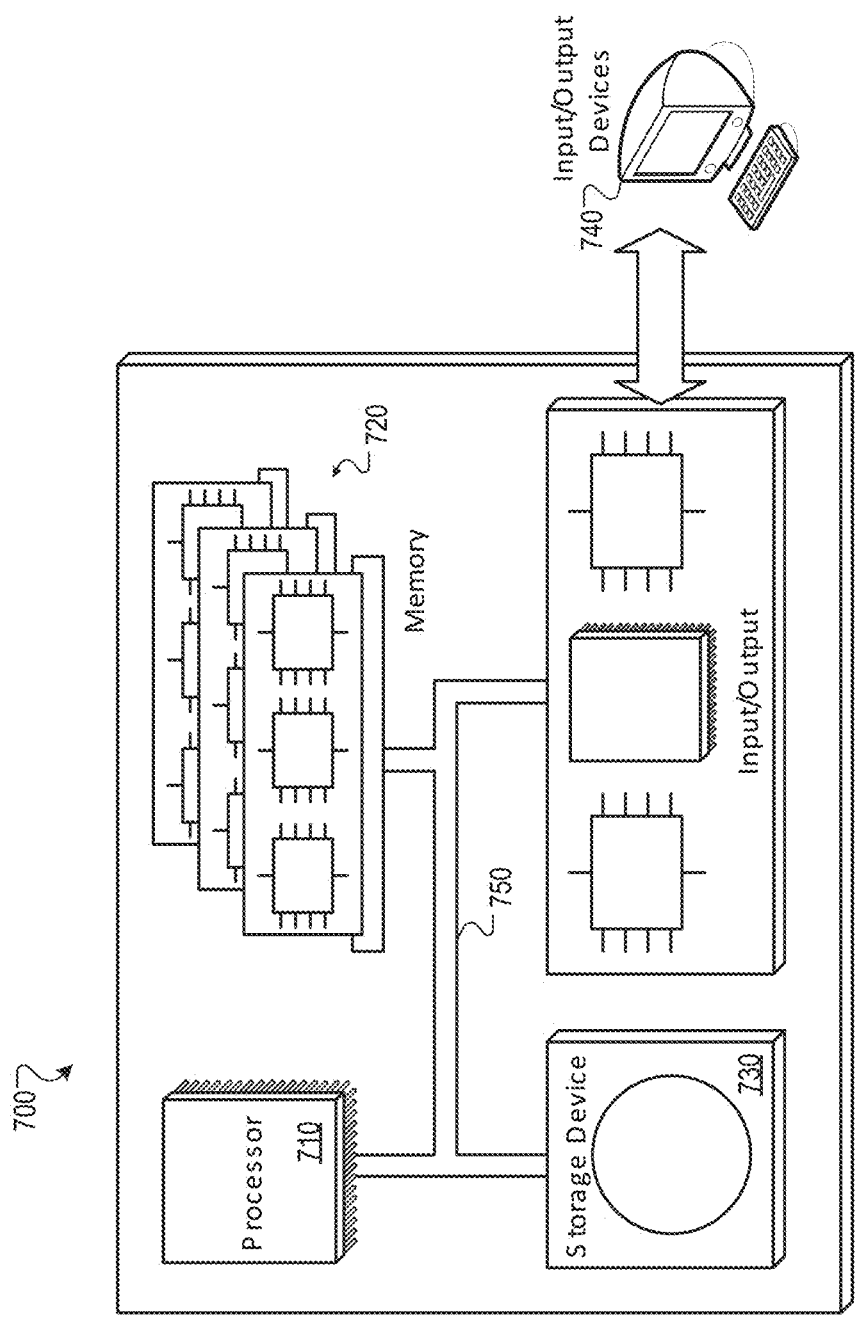
FIG. 7 shows a general computer system that can provide interactivity with a user of a medical device.

The particular techniques described here may be assisted by the use of a computer-implemented medical device, such as a defibrillator that includes computing capability. The computing portions of such defibrillator or other device is shown generally in FIG. 7, and may communicate with and/or incorporate a computer system 700 in performing the operations discussed above, including operations for computing the quality of one or more components of CPR provided to a victim and generating feedback to rescuers, including feedback to change rescuers who are performing certain components of the CPR. The system 700 may be implemented in various forms of digital computers, including computerized defibrillators laptops, personal digital assistants, tablets, and other appropriate computers. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The system 700 includes a processor 710, a memory 720, a storage device 730, and an input/output device 740. Each of the components 710, 720, 730, and 740 are interconnected using a system bus 750. The processor 710 is capable of processing instructions for execution within the system 700. The processor may be designed using any of a number of architectures. For example, the processor 710 may be a CISC (Complex Instruction Set Computers) processor, a RISC (Reduced Instruction Set Computer) processor, or a MISC (Minimal Instruction Set Computer) processor.

In one implementation, the processor 710 is a single-threaded processor. In another implementation, the processor 710 is a multi-threaded processor. The processor 710 is capable of processing instructions stored in the memory 720 or on the storage device 730 to display graphical information for a user interface on the input/output device 740.

The memory 720 stores information within the system 700. In one implementation, the memory 720 is a computer-readable medium. In one implementation, the memory 720 is a volatile memory unit. In another implementation, the memory 720 is a non-volatile memory unit.

The storage device 730 is capable of providing mass storage for the system 700. In one implementation, the storage device 730 is a computer-readable medium. In various different implementations, the storage device 730 may be a floppy disk device, a hard disk device, an optical disk device, or a tape device.

The input/output device 740 provides input/output operations for the system 700. In one implementation, the input/output device 740 includes a keyboard and/or pointing device. In another implementation, the input/output device 740 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having an LCD (liquid crystal display) or LED display for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

Many other implementations other than those described may be employed, and may be encompassed by the following claims.

What is claimed is:

1. A medical system for assisting in resuscitative care of a patient, the medical system comprising:
  a defibrillator having one or more capacitors arranged to provide a defibrillating shock to the patient;
  a plurality of electrodes coupled with the defibrillator and configured to sense an ECG of the patient and to generate ECG signals based on the ECG; and
  one or more computer processors provided with the defibrillator and executable using code and memory stored in a non-transitory computer-readable storage medium, the one or more computer processors being configured to:
    receive the ECG signals from the plurality of electrodes,
    process the ECG signals to generate ECG data,
    perform one or more amplitude spectrum area (AMSA) calculations on the ECG data in a time domain to generate a frequency domain representation of the ECG data and an AMSA transform value based on the frequency domain representation of the ECG data, analyze the ECG data to determine whether a heart rhythm of the patient is shockable, in response to determining that the heart rhythm of the patient is shockable, determine a level of energy to be delivered in a defibrillating shock to the patient based on the AMSA transform value, cause the one or more capacitors to be charged to at least the level of energy to be delivered in the defibrillating shock to the patient, and cause the defibrillator to deliver the defibrillating shock according to the level of energy.

2. The medical system of claim 1, wherein performing the one or more AMSA calculations on the ECG data comprises applying one or more Fast Fourier Transforms (FFTs) to the ECG data.

3. The medical system of claim 2, wherein the one or more FFTs comprise vectorized FFTs applied to vectors formed by an arrangement of the plurality of electrodes.

4. The medical system of claim 2, wherein the one or more AMSA calculations are performed on a window of the ECG data.

5. The medical system of claim 4, wherein the window of the ECG data is between about one second and about 2 seconds in width.

6. The medical system of claim 4, wherein the window of the ECG data is a tapered window.

7. The medical system of claim 1, wherein the one or more computer processors are configured to cause automatic charging of the one or more capacitors to the level of energy to be delivered upon determination of the level of energy.

8. The medical system of claim 1, wherein the frequency domain representation of the ECG data comprises at least one frequency transform value.

9. The medical system of claim 8, wherein the level of energy to be delivered in the defibrillating shock to the patient is based on the frequency transform value.

10. The medical system of claim 1, wherein the level of energy to be delivered in the defibrillating shock to the patient comprises an adjustment from a first level of energy to be delivered to a second level of energy to be delivered.

11. The medical system of claim 1, wherein the one or more computer processors are configured to determine a likelihood of shock success of the patient based on the frequency domain representation of the ECG data.

12. The medical system of claim 1, comprising a visible, audible, or tactile output mechanism arranged to provide an output indication of the level of energy.

13. The medical system of claim 12, wherein the visible, audible, or tactile output mechanism comprises a display module having a screen for presenting the output indication of the level of energy.

14. The medical system of claim 13, wherein the display module is configured to permit user input for using the level of energy to be delivered or for manually selecting a different level of energy to be delivered.

15. The medical system of claim 1, wherein the plurality of electrodes is configured to sense information indicative of a trans-thoracic impedance of the patient and to generate impedance signals based on the information.

16. The medical system of claim 15, comprising a trans-thoracic impedance module configured to receive and process the impedance signals from the plurality of electrodes into an estimated trans-thoracic impedance of the patient.

17. The medical system of claim 16, wherein the one or more computer processors are configured to determine the level of energy to be delivered in the defibrillating shock to the patient based, at least in part, on the estimated trans-thoracic impedance of the patient.

18. The medical system of claim 17, wherein the one or more computer processors are configured to determine the level of energy to be delivered in the defibrillating shock to the patient based on a correlation of the estimated trans-thoracic impedance of the patient and the frequency domain representation of the ECG data.

19. The medical system of claim 1, wherein the one or more computer processors are configured to determine a level of energy to be delivered in a subsequent defibrillating shock to the patient based on the frequency domain representation of the ECG data.

20. The medical system of claim 1, wherein the one or more computer processors are configured to determine a region for employing one of escalating energy levels for a plurality of shocks or a fixed energy level for a plurality of shocks to be delivered.

21. The medical system of claim 1, wherein the defibrillator is a wearable defibrillator.

22. The medical system of claim 1, wherein the level of energy inversely correlates with the AMSA transform value.

23. The medical system of claim 1, wherein the level of energy has a relatively higher value when the AMSA transform value has a relatively lower value.

24. The medical system of claim 1, wherein the level of energy correlates to an elapsed time since receipt of the ECG signals has commenced.

25. The medical system of claim 1, wherein determining the level of energy comprises using a first function for a first set of AMSA transform values below an AMSA threshold and a second function for a second set of AMSA transform values above the AMSA threshold.

26. The medical system of claim 25, wherein the first function comprises a flat function and the second function comprises a slope function.

* * * * *

UNITED STATES PATENT AND TRADEMARK OFFICE
CERTIFICATE OF CORRECTION

PATENT NO. : 10,589,112 B2
APPLICATION NO. : 15/608526
DATED : March 17, 2020
INVENTOR(S) : Weilun Quan and Gary A. Freeman It is certified that error appears in the above-identified patent and that said Letters Patent is hereby corrected as shown below:

On the Title Page

Item (56), Column 2, Line 1 under "OTHER PUBLICATIONS", delete "Fand" and insert -- Fahd --

Signed and Sealed this
Twenty-sixth Day of May, 2020

Andrei Iancu
*Director of the United States Patent and Trademark Office*